US007556925B2

(12) United States Patent
Koide et al.

(10) Patent No.: US 7,556,925 B2
(45) Date of Patent: Jul. 7, 2009

(54) αvβ3 INTEGRIN-BINDING POLYPEPTIDE MONOBODIES AND THEIR USE

(75) Inventors: Shohei Koide, Chicago, IL (US); Stephen Dewhurst, Rochester, NY (US); Akiko Koide, Chicago, IL (US); Julie Richards, Rochester, NY (US); Michelle Miller, Rochester, NY (US)

(73) Assignee: University of Rochester, Rochester, NY (US)

( * ) Notice: Subject to any disclaimer, the term of this patent is extended or adjusted under 35 U.S.C. 154(b) by 495 days.

(21) Appl. No.: 10/473,770

(22) PCT Filed: Apr. 4, 2002

(86) PCT No.: PCT/US02/10763

§ 371 (c)(1), (2), (4) Date: Mar. 9, 2004

(87) PCT Pub. No.: WO02/081497

PCT Pub. Date: Oct. 17, 2002

(65) Prior Publication Data

US 2007/0117966 A1 May 24, 2007

Related U.S. Application Data

(60) Provisional application No. 60/281,481, filed on Apr. 4, 2001.

(51) Int. Cl.

| | |
|---|---|
| *G01N 33/53* | (2006.01) |
| *A61K 39/00* | (2006.01) |
| *A61K 39/385* | (2006.01) |
| *C07K 14/00* | (2006.01) |
| *C07K 1/00* | (2006.01) |

(52) U.S. Cl. .......................... 435/7.1; 435/7.2; 435/7.8; 424/192.1; 424/193.1; 530/350; 530/400

(58) Field of Classification Search ....................... None
See application file for complete search history.

(56) References Cited

U.S. PATENT DOCUMENTS

| | | | | |
|---|---|---|---|---|
| 5,922,676 | A * | 7/1999 | Pasqualini et al. | 514/12 |
| 6,462,189 | B1 | 10/2002 | Koide | |
| 6,673,901 | B2 | 1/2004 | Koide | |
| 6,703,199 | B1 | 3/2004 | Koide | |
| 6,955,900 | B1 * | 10/2005 | Barbas et al. | 435/69.7 |
| 2003/0108948 | A1 | 6/2003 | Koide | |
| 2003/0134386 | A1 | 7/2003 | Koide | |

FOREIGN PATENT DOCUMENTS

| | | | |
|---|---|---|---|
| WO | WO 94/18221 | * | 8/1994 |
| WO | WO 98/56915 | | 12/1998 |
| WO | WO 00/34784 | | 6/2000 |

OTHER PUBLICATIONS

Main et al 1992. Cell 71:671-678.*
Wells, 1990, Biochemistry 29:8509-8517.*
Ngo et al., 1994, The Protein Folding Problem and Tertiary Structure Prediction, Merz et al., eds, Birkhauser, Boston, pp. 491-495.*
Parkhill et al 2001. Nature 413:523-527.*
Koide et al., "Stabilization of a Fibronectin Type III Domain by the Removal of Unfavorable Electrostatic Interactions on the Protein Surface," *Biochemistry* 40:10326-10333 (2001).
Sharma et al., "Specific Interactions Between Human Integrin $\alpha_v\beta_3$ and Chimeric Hepatitis B Virus Core Particles Bearing the Receptor-Binding Epitope of Foot-and-Mouth Disease Virus," *Virology* 239:150-157 (1997).
Koide et al., "The Fibronectin Type III Domain as a Scaffold for Novel Binding Proteins," *J. Mol. Biol.* 284:1141-1151 (1998).
Koide et al., "Probing Protein Conformational Changes in Living Cells By Using Designer Binding Proteins: Application to the Estrogen Receptor," *PNAS* 99(3):1253-1258 (2002).
Arap et al., "Cancer Treatment by Targeted Drug Delivery to Tumor Vasculature in a Mouse Model," Science 279:377-380 (1998).
Brooks et al., "Antiintegrin αvβ3 Blocks Human Breast Cancer Growth and Angiogenesis in Human Skin," J. Clin. Invest. 96:1815-1822 (1995).
Brooks et al., "Integrin αvβ3 Antagonists Promote Tumor Regression by Inducing Apoptosis of Angiogenic Blood Vessels," Cell 79:1157-1164 (1994).
Brooks et al., "Requirement of Vascular Integrin αuβ3 for Angiogenesis," Science 264:569-571 (1994).
Pasqualini et al., "αvIntegrins as Receptors for Tumor Targeting by Circulating Ligands," Nature Biotech. 15:542-546 (1997).
Sipkins et al., "Detection of Tumor Angiogenesis in vivo by αvβ3-Targeted Magnetic Resonance Imaging," Nature Med. 4(5):623-626 (1998).

* cited by examiner

*Primary Examiner*—Manjunath N Rao
*Assistant Examiner*—Shulamith H Shafer
(74) *Attorney, Agent, or Firm*—Nixon Peabody LLP

(57) ABSTRACT

The present invention relates to a polypeptide monobody which includes a modified acid sequence and renders the polypeptide monobody able to bind selectively to αvβ3 integrin. Fusion proteins and conjugates which include the polypeptide monobody, as well as compositions containing the polypeptide monobody, fusion proteins, or conjugates are also disclosed. Uses thereof include: treating or preventing an αvβ3 integrin-mediated disease or disorder, inhibiting αvβ3 integrin activity, treating a cancerous or precancerous condition, imaging tissues using positron emission tomography or magnetic resonance imaging, assessing the metastatic characteristics of a tumor, and delivering DNA to a cell.

31 Claims, 10 Drawing Sheets

```
NdeI
CATATGCAGGTTTCTGATGTTCCGCGTGACCTGGAAGTTGTTGCTGCGACCCCGACTAGC
    MetGlnValSerAspValProArgAspLeuGluValValAlaAlaThrProThrSer
     -2 -1  1                                  10

BclI  PvuII                PstI                              BsiMI
    CTGCTGATCAGCTGGGATGCTCCTGCAGTTACCGTGCGTTATTACCGTATCACGTACGGT
    LeuLeuIleSerTrpAspAlaProAlaValThrValArgTyrTyrArgIleThrTyrGly
             20                         30

EcoRI
    GAAACCGGTGGTAACTCCCCGGTTCAGGAATTCACTGTACCTGGTTCCAAGTCTACTGCT
    GluThrGlyGlyAsnSerProValGlnGluPheThrValProGlySerLysSerThrAla
                40                          50

SalI              Bst1107I
    ACCATCAGCGGCCTGAAACCGGGTGTCGACTATACCATCACTGTATACGCTGTTACTGGC
    ThrIleSerGlyLeuLysProGlyValAspTyrThrIleThrValTyrAlaValThrGly
             60                          70

SacI                                            XbaI
    CGTGGTGACAGCCCAGCGAGCTCCAAGCCAATCTCGATTAACTACCGTACCTAGTAACTC
    ArgGlyAspSerProAlaSerSerLysProIleSerIleAsnTyrArgThr
             80                          90

BamHI
    GAGGATCC
```

Figure 2

```
NdeI                              PstI                              EcoRI
   1         11        21        31        41
MQ  VSDVPRDLEV VAATPTSLLI SWDAPAVTVR YYRITYGETG GNSPVQEFTV
         A         B                    C                 D

SalI              SacI       XhoI
   51        61        71        81        91
    PGSKSTATIS GLKPGVDYTI TVYAVTGRGD SPASSKPISI NYRT
         E             F                        G
```

Figure 3A

```
NdeI                              PstI                              EcoRI
   1         11        21        31        41
MQ  VSDVPRXLEV VAATPTSLLI SWDAPAVTVR YYRITYGETG GNSPVQEFTV
         A         B                    C                 D

SalI              SacI       XhoI
   51        61        71        81        91
    PGSKSTATIS GLKPGVDYTI TVYAVTGRGD SPASSKPISI NYRT
         E             F                        G
```

Figure 3B

| Clone | Sequence | SEQ ID No | Clone | Sequence | SEQ ID No |
|---|---|---|---|---|---|
| 2JCAV1: | LRGDWSED | 5 | 3JCNI1: | PRGDWIEF | 15 |
| 2JCAV2: | VRGDWYEY | 6 | 3JCNI2: | GRGDSPAS | 16 |
| 2JCAV3: | VRGDCSSS | 7 | 3JCNI3: | GRGDDDRL | 17 |
| 2JCAV4: | GRGDLCDF | 8 | 3JCNI4: | GRGDYVLG | 18 |
| 2JCAV5: | GRGDSPAS | 9 | 3JCNI5: | GRGDFSFL | 19 |
| 3JCAV1: | GRGDWTEH | 10 | 3JCLI1: | SRGDVVPP | 20 |
| 3JCAV2: | ARGDWVEG | 11 | 3JCLI2: | TRGDPPPH | 21 |
| 3JCAV3: | PRGDWTEG | 12 | 3JCLI3: | SRGDVVPP | 22 |
| 3JCAV4: | GRGDAFSL | 13 | 3JCLI4: | GRGDWNEG | 23 |
| 3JCAV5: | FRGDSPLD | 14 | 3JCLI5: | FRGDWIEL | 24 | synthetic FN3 gene: GRGDSPAS (SEQ ID No:25)

Figure 4A

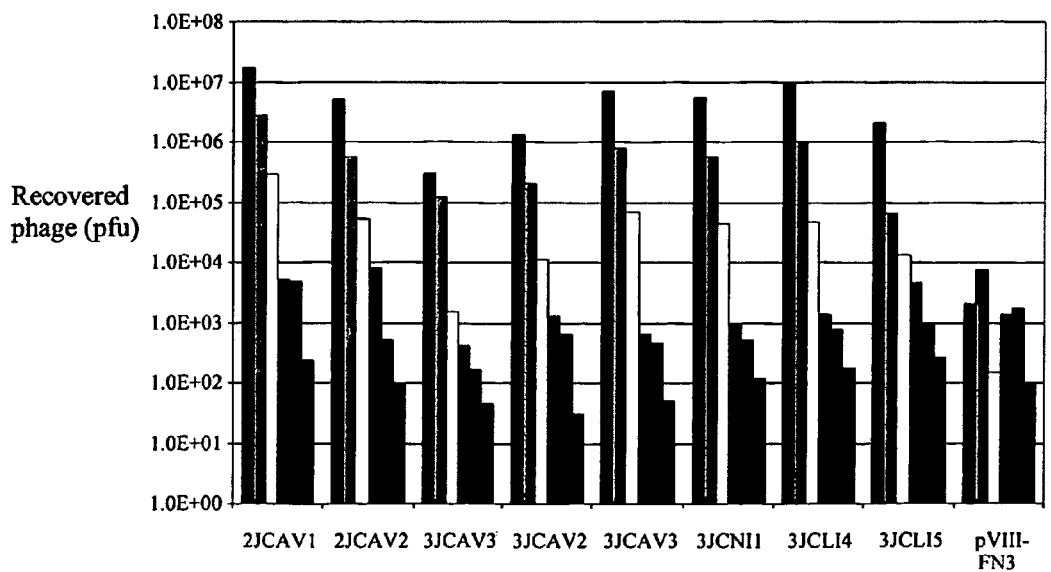

SEQUENCE LISTING

<160> NUMBER OF SEQ ID NOS: 36

<210> SEQ ID NO 1
<211> LENGTH: 308
<212> TYPE: DNA
<213> ORGANISM: Homo sapiens

<400> SEQUENCE: 1

```
catatgcagg tttctgatgt tccgcgtgac ctggaagttg ttgctgcgac cccgactagc        60
ctgctgatca gctgggatgc tcctgcagtt accgtgcgtt attaccgtat cacgtacggt       120
gaaaccggtg gtaactcccc ggttcaggaa ttcactgtac ctggttccaa gtctactgct       180
accatcagcg gcctgaaacc gggtgtcgac tataccatca ctgtatacgc tgttactggc       240
cgtggtgaca gcccagcgag ctccaagcca atctcgatta actaccgtac ctagtaactc       300
gaggatcc                                                                308
```

<210> SEQ ID NO 2
<211> LENGTH: 96
<212> TYPE: PRT
<213> ORGANISM: Homo sapiens

<400> SEQUENCE: 2

```
Met Gln Val Ser Asp Val Pro Arg Asp Leu Glu Val Val Ala Ala Thr
  1               5                  10                  15

Pro Thr Ser Leu Leu Ile Ser Trp Asp Ala Pro Ala Val Thr Val Arg
             20                  25                  30

Tyr Tyr Arg Ile Thr Tyr Gly Glu Thr Gly Gly Asn Ser Pro Val Gln
         35                  40                  45

Glu Phe Thr Val Pro Gly Ser Lys Ser Thr Ala Thr Ile Ser Gly Leu
     50                  55                  60

Lys Pro Gly Val Asp Tyr Thr Ile Thr Val Tyr Ala Val Thr Gly Arg
 65                  70                  75                  80

Gly Asp Ser Pro Ala Ser Ser Lys Pro Ile Ser Ile Asn Tyr Arg Thr
                 85                  90                  95
```

<210> SEQ ID NO 3
<211> LENGTH: 96
<212> TYPE: PRT
<213> ORGANISM: Artificial Sequence
<220> FEATURE:
<223> OTHER INFORMATION: Description of Artificial Sequence:
      polypeptide monobody with mutant tenth fibronectin Fn3 sequence
<220> FEATURE:
<221> NAME/KEY: PEPTIDE
<222> LOCATION: (9)
<223> OTHER INFORMATION: X at position 9 is any non-negatively charged
      amino acid

<400> SEQUENCE: 3

```
Met Gln Val Ser Asp Val Pro Arg Xaa Leu Glu Val Val Ala Ala Thr
 1               5                  10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
            35                  40                  45

Glu Phe Thr Val Pro Gly Ser Lys Ser Thr Ala Thr Ile Ser Gly Leu
        50                  55                  60

Lys Pro Gly Val Asp Tyr Thr Ile Thr Val Tyr Ala Val Thr Gly Arg
65              70                  75                  80

Gly Asp Ser Pro Ala Ser Ser Lys Pro Ile Ser Ile Asn Tyr Arg Thr
                85                  90                  95
```

```
<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: mutant FG
      loop sequence
<220> FEATURE:
<221> NAME/KEY: PEPTIDE
<222> LOCATION: (1)
<223> OTHER INFORMATION: X at position 1 is any amino acid
<220> FEATURE:
<221> NAME/KEY: PEPTIDE
<222> LOCATION: (5)..(8)
<223> OTHER INFORMATION: X at positions 5, 6, 7, and 8 is any amino acid

<400> SEQUENCE: 4

Xaa Arg Gly Asp Xaa Xaa Xaa Xaa
 1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 2JCAV1

<400> SEQUENCE: 5

Leu Arg Gly Asp Trp Ser Glu Asp
 1               5
```

```
<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 2JCAV2

<400> SEQUENCE: 6

Val Arg Gly Asp Trp Tyr Glu Tyr
 1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 2 JCAV3

<400> SEQUENCE: 7
```

```
Val Arg Gly Asp Cys Ser Ser Ser
  1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 2JCAV4

<400> SEQUENCE: 8

Gly Arg Gly Asp Leu Cys Asp Phe
  1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 2JCAV5

<400> SEQUENCE: 9

Gly Arg Gly Asp Ser Pro Ala Ser
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCAV1

<400> SEQUENCE: 10

Gly Arg Gly Asp Trp Thr Glu His
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCAV2

<400> SEQUENCE: 11

Ala Arg Gly Asp Trp Val Glu Gly
  1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCAV3

<400> SEQUENCE: 12

Pro Arg Gly Asp Trp Thr Glu Gly
  1               5

<210> SEQ ID NO 13
<211> LENGTH: 8
<212> TYPE: PRT
<213> ORGANISM: Artificial Sequence
```

```
<220> FEATURE:
<223> OTHER INFORMATION: Description of Artificial Sequence:  FG loop
      sequence of clone 3JCAV4

<400> SEQUENCE: 13

Gly Arg Gly Asp Ala Phe Ser Leu
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCAV5

<400> SEQUENCE: 14

Phe Arg Gly Asp Ser Pro Leu Asp
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCNI1

<400> SEQUENCE: 15

Pro Arg Gly Asp Trp Ile Glu Phe
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCNI2

<400> SEQUENCE: 16

Gly Arg Gly Asp Ser Pro Ala Ser
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCNI3

<400> SEQUENCE: 17

Gly Arg Gly Asp Asp Asp Arg Leu
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence of clone 3JCNI4

<400> SEQUENCE: 18

Gly Arg Gly Asp Tyr Val Leu Gly
 1               5
```

-continued

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 3JCNI5

<400> SEQUENCE: 19

Gly Arg Gly Asp Phe Ser Phe Leu
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of cline 3JCLI1

<400> SEQUENCE: 20

Ser Arg Gly Asp Val Val Pro Pro
  1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 3JCLI2

<400> SEQUENCE: 21

Thr Arg Gly Asp Pro Pro Pro His
  1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 3JCLI3

<400> SEQUENCE: 22

Ser Arg Gly Asp Val Val Pro Pro
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 3JCLI4

<400> SEQUENCE: 23

Gly Arg Gly Asp Trp Asn Glu Gly
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: FG loop
      sequence of clone 3JCLI5

```
<400> SEQUENCE: 24

Phe Arg Gly Asp Trp Ile Glu Leu
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:  synthetic
      Fn3 gene

<400> SEQUENCE: 25

Gly Arg Gly Asp Ser Pro Ala Ser
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:  FG loop
      consensus sequence for avb3 integrin binding
<220> FEATURE:
<221> NAME/KEY: PEPTIDE
<222> LOCATION: (1)
<223> OTHER INFORMATION: X at position 1 can be any amino acid
<220> FEATURE:
<221> NAME/KEY: PEPTIDE
<222> LOCATION: (6)
<223> OTHER INFORMATION: X at position 6 can be any amino acid
<220> FEATURE:
<221> NAME/KEY: PEPTIDE
<222> LOCATION: (8)
<223> OTHER INFORMATION: X at position 8 can be any amino acid

<400> SEQUENCE: 26

Xaa Arg Gly Asp Trp Xaa Glu Xaa
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  control
      RGD peptide

<400> SEQUENCE: 27

Gly Arg Gly Asp Ser Pro Lys
 1               5

<210> SEQ ID NO 28
<211> LENGTH: 309
<212> TYPE: DNA
<213> ORGANISM: Artificial Sequence
<220> FEATURE:
<223> OTHER INFORMATION: Description of Artificial Sequence:  encodes
      polypeptide monobody with mutant FG loop
<220> FEATURE:
<221> NAME/KEY: unsure
<222> LOCATION: (235)..(236)
<223> OTHER INFORMATION: N at positions 235 and 236 is A, G, C, or T
<220> FEATURE:
<221> NAME/KEY: unsure
<222> LOCATION: (237)
<223> OTHER INFORMATION: K at position 237 is G or T
<220> FEATURE:
<221> NAME/KEY: unsure
<222> LOCATION: (247)..(248)
<223> OTHER INFORMATION: N at positions 247 and 248 is A, G, C, or T
```

-continued

```
<220> FEATURE:
<221> NAME/KEY: unsure
<222> LOCATION: (249)
<223> OTHER INFORMATION: K at position is G or T
<220> FEATURE:
<221> NAME/KEY: unsure
<222> LOCATION: (250)..(251)
<223> OTHER INFORMATION: N at positions 250 and 251 is A, G, C, or T
<220> FEATURE:
<221> NAME/KEY: unsure
<222> LOCATION: (252)
<223> OTHER INFORMATION: K at position 252 is G or T
<220> FEATURE:
<221> NAME/KEY: unsure
<222> LOCATION: (253)..(254)
<223> OTHER INFORMATION: N at positions 253 and 254 is A, G, C, or T
<220> FEATURE:
<221> NAME/KEY: unsure
<222> LOCATION: (255)
<223> OTHER INFORMATION: K at position 255 is G or T
<220> FEATURE:
<221> NAME/KEY: unsure
<222> LOCATION: (256)..(257)
<223> OTHER INFORMATION: N at positions 256 and 257 is A, G, C, or T
<220> FEATURE:
<221> NAME/KEY: unsure
<222> LOCATION: (258)
<223> OTHER INFORMATION: K at position 258 is G or T

<400> SEQUENCE: 28
atgcaggttt ctgatgttcc gcgtgacctg aagttgttg ctgcgacccc gactagcctg      60
ctgatcagct gggatgctcc tgcagttacc gtgcgttatt accgtatcac gtacggtgaa    120
accggtggta actccccggt tcaggaattc actgtacctg gttccaagtc tactgctacc    180
atcagcggcc tgaaaccggg tgtcgactat accatcactg tatacgctgt tactnnkcgc    240
ggcgatnnkn nknnknnktc caagccaatc tcgattaact accgtaccgg tggcggttct    300
ggtggcggt                                                            309

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence:   primer
      FN3JCM8Nhe

<400> SEQUENCE: 29
cctagctagc gtagctcagg ccatgcaggt ttctgatgtt c                         41

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence:   FN3JCM8Hin

<400> SEQUENCE: 30
ggccaagctt gaccgccacc agaaccgcca ccggtacggt ag                        42

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:   C-terminal
      tag

<400> SEQUENCE: 31
```

Gly Lys Lys Gly Lys
 1               5

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence:  primer
      FN1F2

<400> SEQUENCE: 32
cgggatccca tatgcaggtt tctgatgttc cgcgtgacct ggaagttgtt gctgcgacc        59

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence:  primer
      FN3GKKGK

<400> SEQUENCE: 33
ccgactcgag ttactattta cctttttac cggtacggta gttaatcgag                   50

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence:  primer
      JCFNFGRGD
<220> FEATURE:
<221> NAME/KEY: unsure
<222> LOCATION: (22)
<223> OTHER INFORMATION: m at position 22 is A or C
<220> FEATURE:
<221> NAME/KEY: unsure
<222> LOCATION: (23)..(24)
<223> OTHER INFORMATION: n at positions 23 and 24 is A, G, C, or T
<220> FEATURE:
<221> NAME/KEY: unsure
<222> LOCATION: (25)
<223> OTHER INFORMATION: m at position 25 is A or C
<220> FEATURE:
<221> NAME/KEY: unsure
<222> LOCATION: (26)..(27)
<223> OTHER INFORMATION: n at positions 26 and 27 is A, G, C, or T
<220> FEATURE:
<221> NAME/KEY: unsure
<222> LOCATION: (28)
<223> OTHER INFORMATION: m at position 28 is A or C
<220> FEATURE:
<221> NAME/KEY: unsure
<222> LOCATION: (29)..(30)
<223> OTHER INFORMATION: n at positions 29 and 30 is A, G, C, or T
<220> FEATURE:
<221> NAME/KEY: unsure
<222> LOCATION: (31)
<223> OTHER INFORMATION: m at position 31 is A or C
<220> FEATURE:
<221> NAME/KEY: unsure
<222> LOCATION: (32)..(33)
<223> OTHER INFORMATION: n at positions 32 and 33 is A, G, C, or T
<220> FEATURE:
<221> NAME/KEY: unsure
<222> LOCATION: (43)
<223> OTHER INFORMATION: m at position 43 is A or C
<220> FEATURE:
<221> NAME/KEY: unsure
<222> LOCATION: (44)..(45)
<223> OTHER INFORMATION: n as positions 44 and 45 is A, G, C, or T

<400> SEQUENCE: 34

```
gttaatcgag attggcttgg amnnmnnmnn mnnatcgccg cgmnnagtaa cagcgtatac          60
```

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: primer
      SFN3F

<400> SEQUENCE: 35

```
agctcaattg gtccggtgga ggttctgatg ttccgcgtga cctg                          44
```

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: primer
      SFN3R

<400> SEQUENCE: 36

```
agctaagctt ttaggtacgg tagttaatcg agat                                     34
```

αvβ3 INTEGRIN-BINDING POLYPEPTIDE MONOBODIES AND THEIR USE

This application is a national stage application under 35 U.S.C. § 371 of PCT/US02/10763, filed Apr. 4, 2002, which claims the benefit of U.S. Provisional Patent Application Ser. No. 60/281,481, filed Apr. 4, 2001, which is hereby incorporated by reference in its entirety.

This invention was made with government support under grant numbers R29-GM55042, T32-AI07362, and T32-GM07356 from the National Institutes of Health; and under grant numbers DAMD17-99-1-9361, DAMD17-01-1-0384, and DAMD17-01-1-0385 from the U.S. Army. The U.S. government has certain rights in this invention.

FIELD OF THE INVENTION

The present invention relates generally to polypeptide monobodies, more particularly polypeptide monobodies derived from the tenth fibronectin type III domain from human fibronectin ("FNfn10") which have activity in binding to αvβ3 integrin, fusion proteins or conjugates which include such a polypeptide monobody, as well as the uses thereof for modulating αvβ3 integrin-mediated activity.

BACKGROUND OF THE INVENTION

αvβ3 (CD51/CD61) is a member of the integrin family of cell surface adhesion receptors. Over 20 different αβ integrin heterodimers exist, each with different tissue and ligand specificities. Normal tissue distribution of αvβ3 is generally limited to high levels of expression on osteoclasts, with lower levels observed on platelets, megakaryocytes, kidney, vascular smooth muscle, placenta, dendritic cells (Weiss et al., 2001), and in varying amounts on normal endothelium (reviewed in Horton, 1997). In contrast to α5β1, which binds to only fibronectin, αvβ3 binds to a wide range of RGD-containing integrin ligands, including but not limited to fibronectin, vitronectin, osteopontin, von Willebrandt factor, and fibrinogen (Horton, 1997).

αvβ3 integrin is a multifunctional cell surface receptor that has pleiotropic roles in normal cell growth and survival. αvβ3 integrin can also contribute to oncogenesis. Consistent with this, upregulation of αvβ3 expression has been observed on the endothelial cells of angiogenic vessels, and binding of αvβ3 to the basement membrane is a critical step in the angiogenesis induced by basic fibroblast growth factor and tumor necrosis factor-α (Friedlander et al., 1995). Expression of αvβ3 has also been implicated in tumor invasion, and it has been shown that αvβ3 binds matrix metalloproteinase-2 (MM-2) and presents MMP-2 on the surface of invasive carcinomas and on invasive angiogenic endothelial cells (Brooks et al., 1996; Silletti et al., 2001).

αvβ3 also regulates cell growth and survival, since ligation of this receptor can, under some circumstances, induce apoptosis in tumor cells (Kozlova et al., 2001). Furthermore, disruption of cell adhesion with anti-αvβ3 antibodies, RGD peptides, and other integrin antagonists has been shown to slow tumor growth (Chatterjee et al., 2000; Chatterjee et al., 2001; and Brooks et al., 1996). Finally, the selective upregulation of αvβ3 expression on tumor blood vessels is also being explored as the basis for imaging of neoplastic lesion, and the αvβ3-specific antibody LM609 has been successfully used for this purpose in vivo (Sipkins et al., 1998).

Novel molecules capable of binding with high specificity to αvβ3 integrin have potential utility in several applications, and as a consequence, αvβ3 has been a frequent target for drug discovery and selection of new binding ligands. Phage display technology, in which combinatorial peptide libraries are expressed on the surface of bacteriophages, has been used to select for peptide ligands capable of binding to αvβ3—yielding a wide range of RGD-containing peptide sequences capable of interacting at moderate affinity with αvβ3 and other integrins (Koivunen et al., 1994; Healy et al., 1995). Phage-displayed random peptide libraries have also been constructed and screened using framework proteins such as the cytotoxic T lymphocyte-associated antigen 4 (CTLA-4). This resulted in the identification of phage clones which could be used to stain human umbilical vein endothelial cells in a flow cytometric assay. However, the ability of the purified recombinant CTLA-4 protein to stain cells, and its cross-reactivity with other integrins was not reported (Hufton et al., 2000).

Fibronectin is a natural ligand of integrins, and it contains repeats of three types of domains. The tenth fibronectin type III domain (FNfn10) includes the RGD sequence in the loop connecting the F and G β-strands (FG loop) (Main et al., 1992). FNfn10 was developed as a scaffold for phage display of peptides because of its small size (94 residues), monomeric assembly, and ability to retain its global fold while exposed loops were randomized (Koide et al., 1998). In addition, FNfn10 lacks cysteine residues and requires no post-translational modification, allowing for large-scale bacterial expression. It has been shown that residues in the FG loop including the RGD sequence are highly flexible (Main et al., 1992; Carr et al., 1997) and this flexibility of the FG loop has been implicated as the origin of the ability of FNfn10 to interact with multiple integrins (Main et al., 1992). While the stability of monobodies makes them well suited for intracellular studies, there has been no prior use of monobodies to probe for modified FG loop or other loop sequences with enhanced binding affinity for and selectivity between integrins, particularly αvβ3 integrin.

The present invention overcomes these and other deficiencies in the art.

SUMMARY OF THE INVENTION

A first aspect of the present invention relates to a polypeptide monobody which includes: at least two Fn3 β-strand domain sequences with a loop region sequence linked between adjacent β-strand domain sequences; and optionally, an N-terminal tail of at least about 2 amino acids, a C-terminal tail of at least about 2 amino acids, or both; wherein at least one loop region sequence, the N-terminal tail, or the C-terminal tail comprises a modified amino acid sequence which varies by deletion, insertion, or replacement of at least two amino acids from a corresponding loop region, N-terminal tail, or C-terminal tail in a wild-type Fn3 domain of fibronectin, and wherein the polypeptide monobody binds selectively to αvβ3 integrin. Compositions containing the polypeptide monobody are also disclosed.

A second aspect of the present invention relates to a nucleic acid molecule encoding a polypeptide monobody of the present invention.

A third aspect of the present invention relates to a DNA construct which includes a DNA molecule encoding a polypeptide monobody of the present invention; a promoter-effective DNA molecule operably coupled 5' of the DNA molecule; and a transcription termination DNA molecule operably coupled 3' of the DNA molecule. Expression vectors and host cells which include the DNA construct are also disclosed.

A fourth aspect of the present invention relates to a fusion protein which includes: a polypeptide monobody of the present invention and a second polypeptide linked by peptide bond to the polypeptide monobody, the second polypeptide being (i) an epitope tag polypeptide, (ii) a detectable marker polypeptide, (iii) a metal ion-complexing polypeptide, or (iv) a DNA-binding polypeptide. Compositions containing the fusion protein are also disclosed.

A fifth aspect of the present invention relates to a fusion protein-metal ion complex which includes a fusion protein of the present invention including a metal ion-complexing polypeptide as the second polypeptide, where the metal ion-complexing polypeptide is complexed with a metal ion.

A sixth aspect of the present invention relates to a fusion protein-DNA complex which includes a fusion protein of the present invention including a DNA-binding polypeptide as the second polypeptide, where the DNA-binding polypeptide is complexed with a DNA molecule via the DNA-binding polypeptide.

A seventh aspect of the present invention relates to a nucleic acid molecule encoding a fusion protein of the present invention.

An eighth aspect of the present invention relates to a DNA construct which includes a DNA molecule encoding a fusion protein of the present invention; a promoter-effective DNA molecule operably coupled 5' of the DNA molecule; and a transcription termination DNA molecule operably coupled 3' of the DNA molecule. Expression vectors and host cells which include the DNA construct as also disclosed.

A ninth aspect of the present invention relates to a conjugate comprising a polypeptide monobody of the present invention conjugated to (i) a chemotherapeutic agent, (ii) a contrasting agent, or (iii) an organic chelating agent. Compositions containing the conjugate are also disclosed.

A tenth aspect of the present invention relates to a method of treating or preventing an αvβ3 integrin-mediated disease or disorder which includes: administering to a patient in need thereof an effective amount of a polypeptide monobody of the present invention which binds to the αvβ3 integrin to inhibit activity thereof, thereby treating or preventing the αvβ3 integrin-mediated disease or disorder.

An eleventh aspect of the present invention relates to a method of treating a cancerous or precancerous condition which includes: administering to a patient in need thereof an effective amount of a polypeptide monobody of the present invention, wherein the polypeptide monobody binds to cancerous or precancerous cells expressing αvβ3 integrin to inhibit αvβ3 integrin-induced activity of the cancerous or precancerous cells.

A twelfth aspect of the present invention relates to a method of treating a cancerous or precancerous condition which includes: administering to a patient in need thereof an effective amount of a conjugate of the present invention, wherein the polypeptide monobody binds to cancerous or precancerous cells expressing αvβ3 integrin to inhibit αvβ3 integrin-induced activity of the cancerous or precancerous cells and delivers the chemotherapeutic agent to the cancerous or precancerous cells.

A thirteenth aspect of the present invention relates to a method of imaging tissues using positron emission tomography or magnetic resonance imaging, the method including: administering a fusion protein-metal ion complex of the present invention to a patient and detecting, by positron emission tomography or magnetic resonance imaging, whether the complex is localized within any tissues of the patient.

A fourteenth aspect of the present invention relates to a method of imaging tissues using positron emission tomography or magnetic resonance imaging, the method including: administering to a patient a conjugate of the present invention which includes a contrasting agent and detecting, by positron emission tomography or magnetic resonance imaging, whether the conjugate is localized within any tissues of the patient.

A fifteenth aspect of the present invention relates to a method of assessing the metastatic characteristics of a tumor, the method including: administering a fusion protein-metal ion complex of the present invention to a patient and detecting, by positron emission tomography or magnetic resonance imaging, whether the conjugate is localized within any tissues of the patient, wherein localization of the fusion protein-metal ion complex indicates an angiogenic site containing a potentially metastatic tumor.

A sixteenth aspect of the present invention relates to a method of assessing the metastatic characteristics of a tumor, the method including: administering to a patient a conjugate of the present invention which includes a contrasting agent and detecting, by positron emission tomography or magnetic resonance imaging, whether the conjugate is localized within any tissues of the patient, wherein localization of the fusion protein-metal ion complex indicates an angiogenic site containing a potentially metastatic tumor.

A seventeenth aspect of the present invention relates to a method of inhibiting αvβ3 integrin activity which includes: contacting αvβ3 integrin with a polypeptide monobody of the present invention under conditions effective to inhibit the activity of the αvβ3 integrin.

An eighteenth aspect of the present invention relates to a method of delivering DNA to a cell which includes: providing a fusion protein-DNA complex of the present invention and contacting a cell expressing an αvβ3 integrin with the fusion protein-DNA complex under conditions effective to cause uptake of the fusion protein-DNA complex, thereby delivering the DNA into the cell.

A nineteenth aspect of the present invention relates to an isolated polypeptide which binds to an αvβ3 integrin and includes the amino acid sequence XRGDWXEX where X is any amino acid (SEQ ID No: 26).

The structure of the polypeptide monobodies of the present invention are advantageous for multiple applications because they (1) lack disulfide bonds, rendering them resistant against reducing agents; (2) are very stable even at high temperature; and (3) can be produced in a bacterial expression system with yields of up to 50-100 mg per liter of culture. Moreover, because they are derived from the endogenous human protein fibronectin, which is non-immunogenic, it is believed that the polypeptide monobodies will not elicit an immune response. As a small, single-chain molecule, DNA encoding the polypeptide monobodies can be incorporated into gene delivery vectors (e.g. viral vectors, liposomes) for cell or tissue-specific gene expression. As a result of these properties, the polypeptide monobodies of the present invention can be used to treat or prevent a number of αvβ3 integrin-associated diseases or disorders as well as for diagnostic imaging of αvβ3 integrin-expressing tissues.

BRIEF DESCRIPTION OF THE DRAWINGS

FIG. 2 illustrates a nucleotide sequence (SEQ ID No: 1) encoding the amino acid sequence (SEQ ID No: 2) of the wild-type FNfn10. The amino acid numbering is according to Main et al. (1992). The BC loop region and the FG loop region are shown in boxes.

FIGS. 3A-B illustrate the amino acid sequence of the wild-type FNfn10 (SEQ ID No: 2, FIG. 3A) as well as a mutant FNfn10 (SEQ ID No: 3, FIG. 3B) which has the Asp-7 residue replaced with a non-negatively charged amino acid residue (X), which is preferably either Asn or Lys. As reported in Koide et al. (2001), both of these mutations have the effect of promoting greater stability of the mutant FNfn10 at neutral pH as compared to the wild-type FNfn10.

FIGS. 4A-B illustrate the FG loop sequences used during phage display screening of a JCFN-RGD library. M13 Phage displaying a library of FNfn10 clones with partially randomized FG loops (XRGDXXXX, SEQ ID No: 4) were amplified using 0.0, 0.1, or 1 mM IPTG to vary FNfn10 copy number on the phage. Amplified phage populations were subjected to three rounds of biopanning against wells coated with αvβ3 integrin (5 μg/ml). FIG. 4A shows the FG loop sequences for five clones, each of which was sequenced from the second round eluate of the library amplified with 1 mM IPTG (2JCAV1-2JCAV5, SEQ ID Nos: 5-9), from the third round eluate of the library amplified with 1 mM IPTG (3JCAV1-5, SEQ ID Nos: 10-14), from the third round eluate of the library amplified with low IPTG (3JCLI1-5, SEQ ID Nos: 15-19), and from the third round eluate of the library amplified with no IPTG (3JCNI1-5, SEQ ID Nos: 20-24). FIG. 4B illustrates the phage binding assay of the phage clones containing the XRGDWXEX consensus (SEQ ID No: 26) and unmodified FNfn10 (pVIII-FNfn10), all amplified without IPTG. Phage inputs of $10^9$, $10^8$, or $10^7$ pfu were added to wells coated with 5 μg/ml αvβ3 (solid bars) or 0.5 mg/ml BSA (patterned bars). After one hour, nonbinding phage were removed by extensive rinsing and bound phage were eluted with 0.2M glycine, pH 2.2. Eluates from each well were titered. Results shown are representative of three different experiments that yielded similar results.

In FIGS. 5A-D, the experiments shown are all representative of three different experiments that yielded similar results.

FIG. 6A illustrates the binding competition with unlabelled FNfn10-3JCLI4 (◆) or unlabelled FNfn10-WT (■). FIG. 6B illustrates the binding competition with unlabelled FNfn10-3JCLI4 (▲), echistatin (■), and GRGDSPK peptide (◆)(SEQ ID No: 27).

FIG. 7A is a histogram plot of flow cytometric staining analysis of K562 and K562-αvβ3 cells using FNfn10-3JCLI4. FIG. 7B shows mean APC fluorescence for integrin-transfected K562 cells stained with biotinylated FNfn10-3JCLI4 (dark bars) or FNfn10-WT (light bars). To determine the effect of high temperature on FNfn10-3JCLI4 stability, 1 μg/ml 3JCLI4 (◆) or 5 μg/ml LM609 (■) were incubated for 24 hours in FACS buffer at 4, 20, 37, 50, 65, or 75° C. (FIG. 7C). $10^5$ K562-αvβ3 cells were pelleted for each sample and re-suspended in the appropriately treated FNfn10-3JCLI4 or LM609, followed by detection as above.

In FIG. 8A, adhesion of binding of K562-αvβ3 cells to vitronectin is shown. Inhibitors added include FNfn10-3JCLI4, FNfn10-WT, and LM609 antibody, at the stated final concentrations. The lane marked "no αvβ3" corresponds to control K562 cells (no αvβ3), while "no VN" denotes cell adherence (K562-αvβ3 cells) measured on control wells (no vitronectin); the lane marked "NT" corresponds to K562-αvβ3 cells which were bound to vitronectin in the absence of any competitor. In FIG. 8B, adhesion of K562-αvβ3 cells to vitronectin is shown. Echistatin (■) and FNfn10-3JCLI4 (♦) were added at final concentrations of 400, 40, and 4 nM, prior to addition of the cells and initiation of the binding assay. Binding is expressed as a percentage of the O.D.$_{570}$ recorded for K562-αvβ3 adhesion in the absence of competitor, and a background subtraction was performed for all data points, which corresponded to the measured O.D.$_{570}$ for BSA-coated wells (no integrin). In FIG. 8C, adhesion of K562-αIIbβ3 cells to fibronectin is shown. Echistatin (■) and FNfn10-3JCLI4 (♦) were added at final concentrations of 400, 40, and 4 nM prior to addition of the cells and initiation of the binding assay. Binding is expressed as a percentage of the O.D.$_{570}$ recorded for K562-αIIbβ3 adhesion in the absence of competitor, and a background subtraction was performed for all data points, which corresponded to the measured O.D.$_{570}$ for BSA-coated wells (no integrin).

DETAILED DESCRIPTION OF THE INVENTION

Figure 1:
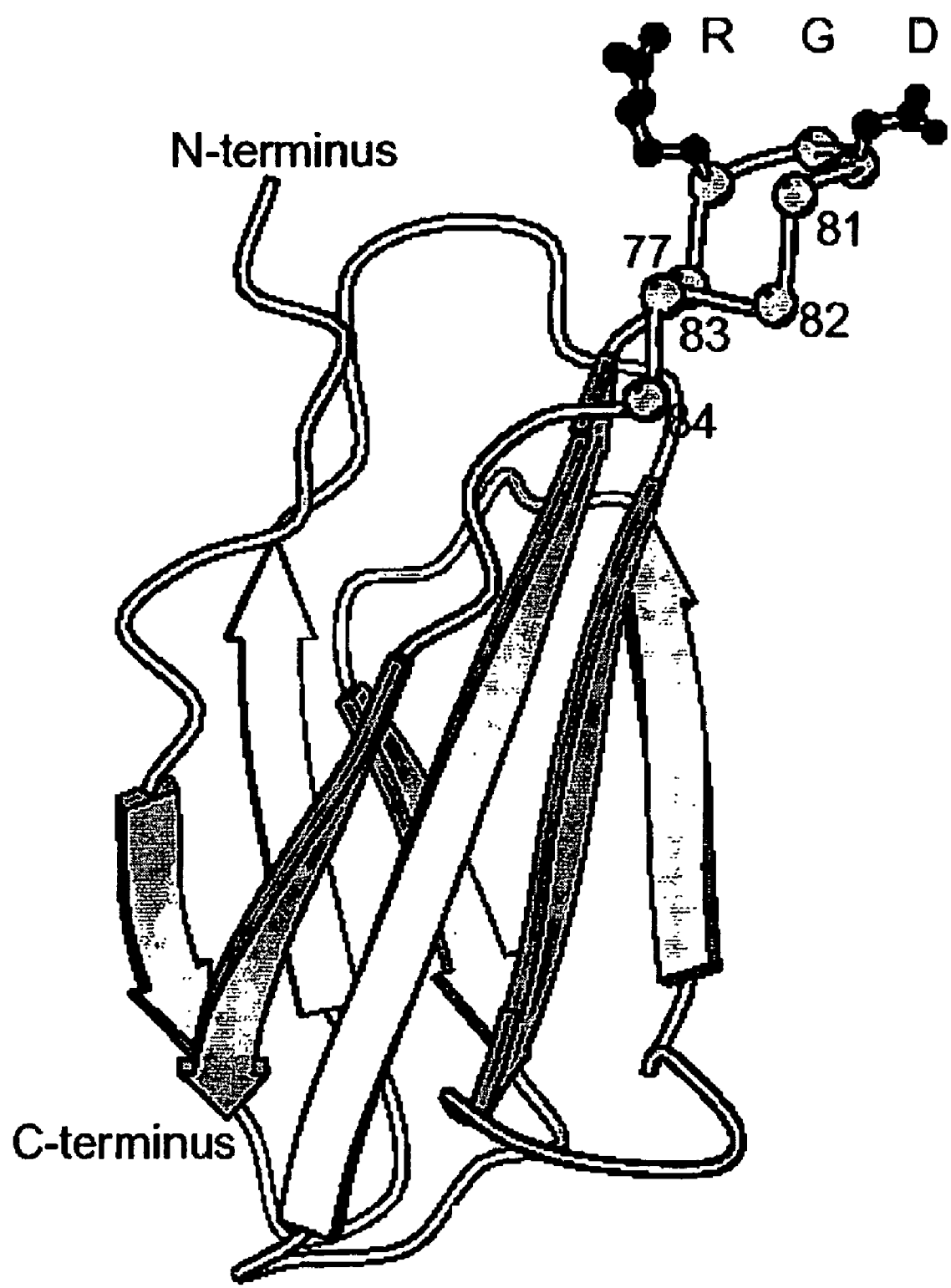
FIG. 1 is a schematic drawing of FNfn10 (Main et al., 1992) showing the RGD sequence and the positions of residues in the FG loop that were diversified in the JCFNRGD library. This figure was made with the program MOLSCRIPT (Kraulis, 1991).

As used herein, "polypeptide monobody" is intended to mean a polypeptide which includes a β-strand domain lacking in disulfide bonds and containing a plurality of β-strands, two or more loop regions each connecting one β-strand to another β-strand, and optionally an N-terminal tail, a C-terminal tail, or both, wherein at least one of the two or more loop regions, the N-terminal tail, or the C-terminal tail is characterized by activity in binding a target protein or molecule. More specifically, such polypeptide monobodies of the present invention can include three or more loop regions or, even more specifically, four or more loop regions. The size of such polypeptide monobodies is preferably less than about 30 kDa, more preferably less than about 20 kDa.

The polypeptide monobodies of the present invention are also characterized by specificity for binding to αvβ3 integrin (i.e., enhanced binding specificity for αvβ3 integrin over other integrins, as compared to wild type polypeptide monobodies or wild type fibronectin). To achieve the specificity in their binding to αvβ3 integrin, the amino acid sequence of the polypeptide monobody has been modified relative to the scaffold used for its construction.

Scaffolds for formation of a polypeptide monobody should be highly soluble and stable. It is small enough for structural analysis, yet large enough to accommodate multiple binding domains so as to achieve tight binding and/or high specificity for its target.

An exemplary scaffold for formation of a polypeptide monobody is the fibronectin type III domain (Fn3). Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily (Fn3 family or s-type Ig family) of the immunoglobulin superfamily. The Fn3 family includes cell adhesion molecules, cell surface hormone and cytokine receptors, chaperoning, and carbohydrate-binding domains (for reviews, see Bork & Doolittle, 1992; Jones, 1993; Bork et al., 1994; Campbell & Spitzfaden, 1994; Harpez & Chothia, 1994).

Crystallographic studies have revealed that the structure of the DNA binding domains of the transcription factor NF-kB is also closely related to the Fn3 fold (Ghosh et al., 1995; Müller et al., 1995). These proteins are all involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., 1992) and by X-ray crystallography (Leahy et al., 1992; Dickinson et al., 1994). The structure is best described as a β-sandwich similar to that of antibody VH domain except that Fn3 has seven β-strands (see FIG. 1) instead of nine. There are three loops on each end of Fn3; the positions of the BC, DE, and FG loops approximately correspond to those of CDR 1, 2 and 3 of the VH domain.

Fn3 is small (~94 residues), monomeric, soluble, and stable. It is one of few members of IgSF that do not have disulfide bonds and, therefore, is stable under reducing conditions. Fn3 has been expressed in *E. Coli* (Aukhil et al., 1993). In addition, 17 Fn3 domains are present just in human fibronectin, providing important information on conserved residues which are often important for the stability and folding (see Main et al., 1992; Dickinson et al., 1994). From sequence analysis, large variations are seen in the BC and FG loops, suggesting that the loops are not crucial to stability. NMR studies have revealed that the FG loop is highly flexible; the flexibility has been implicated for the specific binding of the 10th Fn3 to α$_5$β$_1$ integrin through the Arg-Gly-Asp (RGD) motif In the crystal structure of human growth hormone-receptor complex (de Vos et al., 1992), the second Fn3 domain of the receptor interacts with growth hormone via the FG and BC loops, suggesting it is feasible to build a binding site using the two loops.

The tenth type III module of fibronectin has a fold similar to that of immunoglobulin domains, with seven β strands forming two antiparallel β sheets, which pack against each other (FIG. 1; Main et al., 1992). The structure of the type H module includes seven β strands, which form a sandwich of two antiparallel sheets, one containing three strands (ABE) and the other four strands (C'CFG) (Williams & Barclay, 1988). The β sheet contains residues Glu-9-Thr-14 (A), Ser-17-Asp-23 (B), and Thr-56-Ser-60 (E). The majority of the conserved residues contribute to the hydrophobic core, with the invariant hydrophobic residues Trp-22 and Try-68 lying toward the N-terminal and C-terminal ends of the core, respectively. The β strands are much less flexible and appear to provide a rigid framework upon which functional, flexible loops can be built. The topology is similar to that of immunoglobulin C domains.

Preferred polypeptide monobodies of the present invention are fibronectin type III (Fn3)-derived polypeptide monobodies. Fn3 monobodies include at least two Fn3 β-strand domain sequences with a loop region sequence linked between adjacent β-strand domain sequences and optionally, an N-terminal tail of at least about 2 amino acids, a C-terminal tail of at least about 2 amino acids, or both. The loop region sequence, the N-terminal tail, or the C-terminal tail, or combinations thereof include an amino acid sequence which has binding specificity for αvβ3 integrin. To render a loop region sequence, N-terminal tail, or C-terminal tail capable of binding to αvβ3 integrin, either the loop region sequence, the N-terminal tail, the C-terminal tail, or a combination thereof varies by deletion, insertion, or replacement of at least two amino acids from a corresponding loop region, N-terminal tail, or C-terminal tail in a wild-type or mutant Fn3 scaffold.

One preferred wild-type Fn3 scaffold is the tenth Fn3 domain of human fibronectin (FNfn10), which has an amino acid sequence according to SEQ ID No: 2 (FIG. 3A). One preferred mutant Fn3 scaffold is the tenth Fn3 domain of human fibronectin which has a modified Asp7, which is replaced by a non-negatively charged amino acid residue (i.e., Asn, Lys, etc.) as shown in FIG. 3B (SEQ ID No: 3). As reported in Koide et al. (2001), both of these mutations have the effect of promoting greater stability of the mutant FNfn10 at neutral pH as compared to the wild-type FNfn10.

Both the mutant and wild-type FNfn10 are characterized by the same structure, namely seven β-strand domain sequences (designated A through G) and six loop regions (AB loop, BC loop, CD loop, DE loop, EF loop, and FG loop) which connect the seven β-strand domain sequences. In SEQ ID Nos: 2 and 3, the AB loop corresponds to residues 15-16, the BC loop corresponds to residues 22-30, the CD loop corresponds to residues 39-45, the DE loop corresponds to residues 51-55, the EF loop corresponds to residues 60-66, and the FG loop corresponds to residues 76-87. As shown in FIG. 1, the BC loop, DE loop, and FG loop are all located at the same end of the polypeptide monobody.

According to one particular embodiment, the preferred polypeptide monobodies are mutant or wild-type FNfn10 scaffolds which include a modified FG loop region, which polypeptide monobodies exhibit increased activity in binding to αvβ3 integrin. Such binding is preferably selective of αvβ3 integrin over other integrins. The modified FG loop region preferably includes an amino acid sequence including XRGDWXEX (SEQ ID No: 26), where X is any amino acid residue.

The polypeptide monobodies of the present invention can be prepared by recombinant techniques, thereby affording the deletion, insertion, or replacement of at least two amino acids from a corresponding loop region, N-terminal tail, or C-terminal tail in a wild-type or mutant Fn3 scaffold. Deletions can be a deletion of at least two amino acid residues up to substantially all but one amino acid residue appearing in a particular loop region or tail. Insertions can be an insertion of at least two amino acid residues up to about 25 amino acid residues, preferably at least two up to about 15 amino acid residues. Replacements can be replacements of at least two up to substantially all amino acid residues appearing in a particular loop region or tail. The polypeptide monobodies preferably possess an amino acid sequence which is at least 50% homologous to a β-strand domain of the FNfn10.

The deletions, insertions, and replacements (relative to wild-type or previously known mutant) on Fn3 scaffolds can be achieved using recombinant techniques beginning with a known nucleotide sequence. A synthetic gene for the tenth Fn3 of human fibronectin (FIG. 2) was designed which includes convenient restriction sites for ease of mutagenesis and uses specific codons for high-level protein expression (Gribskov et al., 1984). This gene is substantially identical to the gene disclosed in co-pending U.S. patent application Ser. No. 09/096,749 to Koide filed Jun. 12, 1998, which is hereby incorporated by reference in its entirety.

The gene was assembled as follows: first the gene sequence was divided into five parts with boundaries at designed restriction sites (FIG. 2); for each part, a pair of oligonucleotides that code opposite strands and have complementary overlaps of about 15 bases was synthesized; the two oligonucleotides were annealed and single strand regions were filled in using the Klenow fragment of DNA polymerase; the double-stranded oligonucleotide was cloned into the pET3a vector (Novagen) using restriction enzyme sites at the termini of the fragment and its sequence was confirmed by an Applied Biosystems DNA sequencer using the dideoxy termination protocol provided by the manufacturer; and these steps were repeated for each of the five parts to obtain the whole gene. Although this approach takes more time to assemble a gene than the one-step polymerase chain reaction (PCR) method (Sandhu et al., 1992), no mutations occurred in the gene. Mutations would likely have been introduced by the low fidelity replication by Taq polymerase and would have required time-consuming gene-editing. Recombinant DNA manipulations were performed according to Molecular Cloning (Sambrook et al., 1989), unless otherwise stated. To avoid the introduction of mutations during one-step PCR, high fidelity/low error polymerases can be employed as is known in the art.

Desired mutations can be introduced to the Fn3 gene using either cassette mutagenesis, oligonucleotide site-directed mutagenesis techniques (Deng & Nickoloff, 1992), or Kunkel mutagenesis (Kunkel et al., 1987).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis. Regardless of the approach utilized to introduce mutations into the monobody nucleotide sequence, sequencing can be performed to confirm that the designed mutations (and no other mutations) were introduced by mutagenesis reactions.

In contrast, Kunkel mutagenesis can be utilized to randomly produce a plurality of mutated monobody coding sequences which can be used to prepare a combinatorial library of polypeptide monobodies for screening. Basically, targeted loop regions (or C-terminal or N-terminal tail regions) can be randomized using the NNK codon (N denoting a mixture of A, T, G, C, and K denoting a mixture of G and T) (Kunkel et al., 1987).

An exemplary DNA molecule encoding a mutant Fn3 polypeptide monobody is set forth as SEQ ID No: 28 below:

```
atgcaggttt ctgatgttcc gcgtgacctg gaagttgttg ctgcgacccc gactagcctg    60
ctgatcagct gggatgctcc tgcagttacc gtgcgttatt accgtatcac gtacggtgaa   120
accggtggta actccccggt tcaggaattc actgtacctg gttccaagtc tactgctacc   180
```

```
                                    -continued
atcagcggcc tgaaaccggg tgtcgactat accatcactg tatacgctgt tactnnkcgc 240
ggcgatnnkn nknnknnktc caagccaatc tcgattaact accgtaccgg tggcaggttct 300 ggtggcggt                                                        309
```

In the above DNA sequence, codons nt 235-237, nt 247-249, nt 250-252, nt 253-255, and nt 256-258 (bold typeface) encode random amino acid residues within the FG loop. According to the preferred embodiments of the present invention, however, codons nt 247-249 and nt 253-255 encode, respectively tryptophan and glutamic acid. The seven codons extending from nt 230-250 encode a seven residue linker which, though not required for formation of a polypeptide monobody of the present invention, is useful in forming fusion proteins as described below.

Regardless of the approach used to prepare the nucleic acid molecules encoding the polypeptide monobody, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences.

Alternatively, a recombinant gene or DNA construct can be prepared prior to its insertion into an expression vector. For example, using conventional recombinant DNA techniques, a promoter-effective DNA molecule can be operably coupled 5' of a DNA molecule encoding the polypeptide monobody and a transcription termination (i.e., polyadenylation sequence) can be operably coupled 3' thereof.

U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant molecules can be introduced into cells via transformation, particularly transduction, conjugation, mobilization, or electroporation. The DNA sequences are cloned into the vector using standard cloning procedures in the art, as described by Sambrook et al. (1989).

A variety of host-vector systems may be utilized to express the polypeptide monobody or fusion protein which includes a polypeptide monobody. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; and mammalian cell systems infected with virus (e.g., vaccinia virus, adenovirus, etc.). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters may not be recognized in or may not function in eukaryotic cells. Promoters suitable for use in each of these systems are well known in the art.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts & Lauer (1979).

In addition, polyadenylation signals suitable for use in a desired host cell can also be employed to effect appropriate translation of the DNA molecule (encoding the polypeptide monobody of the present invention. Polyadenylation signals suitable for use in each of the above-identified systems are well known in the art.

Basically, the DNA molecule encoding the polypeptide monobody is ligated to the appropriate promoter and polyadenylation sequences using conventional recombinant techniques, with the promoter being located upstream or 5' to the DNA molecule and the polyadenylation signal being located downstream or 3' of the DNA molecule. As a result of ligating the DNA molecule to the promoter and polyadenylation signal sequences, a DNA construct of the present invention is formed. This DNA construct can be cloned directly into a suitable expression vector (e.g., plasmid, viral DNA, etc.) or it can be formed upon cloning the DNA molecule into an empty expression vector which includes an appropriate restriction site intermediate the promoter and polyadenylation signals which are present in the empty vector.

Once the DNA molecule encoding the polypeptide monobody has been cloned into an expression system, it is ready to be incorporated into a host cell. Such incorporation can be carried out by the various forms of transformation noted above, depending upon the vector/host cell system. Suitable host cells include, but are not limited to, bacteria, yeast cells, mammalian cells, etc. Upon growing the host cells in a suitable growth medium, the host cells are encouraged to express the polypeptide monobodies of the present invention.

In at least several of the various uses of the polypeptide monobodies of the present invention, discussed infra, it is often desirable for the polypeptide monobodies to be produced in substantially purified form, particularly when their administration to a patient is contemplated. Purification can be carried out according to previously reported procedures, which involve metal affinity chromatography for monobodies containing a poly-histidine tag (see Koide et al., 1998).

Another aspect of the present invention relates to a polypeptide (i.e., whether in the form of a polypeptide monobody or not) which includes the amino acid sequence RGD-WXE (amino acid residues 2-7 of SEQ ID No: 26) and selectively binds αvβ3 integrin over other integrins. Such a polypeptide can be prepared, isolated, and purified according to known procedures. Typically, this involves recombinant expression of the desired polypeptide monobody by a host cell, propagation of the host cells, lysing the host cells, and recovery of supernatant by centrifugation to remove host cell debris. The supernatant can be subjected to sequential ammonium sulfate precipitation. The fraction containing the polypeptide monobodies of the present invention is then subjected to gel filtration in an appropriately sized dextran or polyacrylamide column to separate the polypeptide monobodies. If necessary, the protein fraction may be further purified by HPLC.

A further aspect of the present invention relates to fusion proteins which include a polypeptide or polypeptide monobody of the present invention and a second polypeptide linked by peptide bond to the polypeptide or polypeptide monobody. The second polypeptide can be (i) an epitope tag polypeptide, e.g., polyhistidine, (ii) a detectable marker polypeptide, e.g., alkaline phosphatase, (iii) a metal ion-complexing polypeptide, or (iv) a DNA-binding polypeptide, e.g., polylysine. Each of these fusion proteins can be prepared using recombinant techniques described above to form an in-frame gene fusion that can be expressed in appropriate host cells. Thereafter, the fusion protein can isolated and purified using the techniques described above.

Once the polypeptides, polypeptide monobodies, or fusion proteins have been obtained in isolated or, more preferably, purified form, they can be used for therapeutic, preventative, or diagnostic purposes as described hereinafter. Because the polypeptides and polypeptide monobodies of the present invention are capable of binding αvβ3 integrin selectively, they can be used for therapeutic, preventative, or diagnostic purposes, or to modify αvβ3 integrin activity. Although references below are made to use of the polypeptide or polypeptide monobody, it should be appreciated that the polypeptide or polypeptide monobody can also be in the form of a fusion protein or conjugate as described elsewhere herein.

Thus, one aspect of the present invention relates to a method of treating or preventing an αvβ3 integrin-mediated disease or disorder which includes administering to a patient in need thereof, an effective amount of a polypeptide or polypeptide monobody of the present invention which selectively binds to αvβ3 integrin, thereby treating or preventing the αvβ3 integrin-mediated disease or disorder. Such administration is carried out under conditions which are effective to treat or prevent the αvβ3 integrin-mediated disease or disorder. Typically, this includes administering the polypeptide or polypeptide monobody to the patient in a manner effective to contact one or more cells expressing αvβ3 integrin with a sufficient amount of the polypeptide or polypeptide monobody to inhibit the activity of αvβ3 integrin on such one or more cells. As a result of such inhibition, the αvβ3 integrin-mediated diseases or disorders are treated or prevented.

For therapeutic or preventative treatments, the patient can be any mammal which expresses αvβ3 integrin, preferably though not exclusively humans.

Integrins are a group of cell surface glycoproteins that mediate cell adhesion and therefore are mediators of cell adhesion interactions that occur in various biological processes. Integrins are heterodimers composed of noncovalently linked α and β polypeptide subunits. Currently at least eleven different α subunits have been identified and at least six different β subunits have been identified. The various α subunits can combine with various β subunits to form distinct integrins.

The integrin identified as αvβ3 (also known as the vitronectin receptor) has been identified as an integrin that plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that integrin inhibiting agents would be useful as antivirals, antifungals and antimicrobials. Thus, polypeptides or polypeptide monobodies that selectively bind αvβ3 integrin, thereby inhibiting αvβ3 integrin-mediated conditions, would be beneficial for treating or preventing such conditions.

It has been shown that the αvβ3 integrin binds to a number of Arg-Gly-Asp (RGD) containing matrix macromolecules, such as fibrinogen (Bennett et al., 1983), fibronectin (Ginsberg et al., 1983), and von Willebrand factor (Ruggeri et al., 1982). Compounds containing the RGD sequence mimic extracellular matrix ligands so as to bind to cell surface receptors. However, it is also known that RGD peptides in general are non-selective for RGD dependent integrins. For example, most RGD peptides that bind to αvβ3 also bind to αvβ5, αvβ1, and αIIbβIIIa. Antagonism of platelet αIIbβIIIa (also known as the fibrinogen receptor) is known to block platelet aggregation in humans. In order to avoid bleeding side-effects when treating the conditions of disease states associated with the integrin αvβ3, it would be beneficial to develop agents which selectively bind to αvβ3 as opposed to αIIbβIIIa as well as other integrins. Polypeptides or polypeptide monobodies selective for αvβ3 offer such an advantage.

As noted above, integrins are believed to be involved in, among other biological processes, tumor metastasis and neoplasia. Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor. Studies have shown (Humphries et al., 1988), that RGD-like compounds can interfere with experimental metastasis wherein tumor cells are injected directly into the blood. In addition, Seftor et al. (1992) have shown that the αvβ3 integrin has a biological function in melanoma cell invasion. Montgomery et al., (1994) demonstrated that the integrin αvβ3 expressed on human melanoma cells promotes a survival signal, protecting the cells from apoptosis. Accordingly, mediation of the tumor cell metastatic pathway by interference with the αvβ3 integrin cell adhesion receptor to impede tumor metastasis would be beneficial. Brooks et al. (1994a) have demonstrated that antagonists of αvβ3 provide a therapeutic approach for the treatment of neoplasia (inhibition of solid tumor growth) since systemic administration of αvβ3 antagonists causes dramatic regression of various histologically distinct human tumors.

The adhesion receptor integrin αvβ3 was also identified as a marker of angiogenic blood vessels in chick and man and plays a critical role in angiogenesis or neovascularization (Brooks et al., 1995). Angiogenesis is characterized by the invasion, migration and proliferation of smooth muscle and endothelial cells. Antagonists of αvβ3 inhibit this process by selectively promoting apoptosis of cells in neovasculature. The growth of new blood vessels, or angiogenesis, also contributes to pathological conditions such as diabetic retinopathy (Adonis et al., 1994), rheumatoid arthritis (Peacock et al., 1992) and osteoarthritis (Ondrick et al., 1992). Therefore, αvβ3 antagonists are useful targets for treating or preventing such conditions associated with neovascularization (Brooks et al., 1994b). Because angiogenesis occurs normally in the female reproductive organs, antagonists of αvβ3 would be useful in controlling fertility.

It has also been reported that the cell surface receptor αvβ3 is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of αvβ3 have been shown to be potent inhibitors of osteoclastic activity both in vitro (Sato et al., 1990) and in vivo (Fisher et al., 1993). Antagonism of αvβ3 leads to decreased bone resorption and therefore restores a normal balance of bone forming and resorbing activity. Thus, it would be beneficial to provide antagonists of osteoclast αvβ3 which are effective inhibitors of bone resorption and, therefore, are useful in the treatment or prevention of osteoporosis.

The role of the αvβ3 integrin in smooth muscle cell migration also makes it a therapeutic target for prevention or inhibition of neointimal hyperplasia which is a leading cause of restenosis after vascular procedures (Choi et al., 1994). Prevention or inhibition of neointimal hyperplasia (restenosis) by the polypeptides or polypeptide monobodies of the present invention will be beneficial.

White (1993) has reported that adenovirus uses αvβ3 for entering host cells. The integrin appears to be required for endocytosis of the virus particle and may be required for penetration of the viral genome into the host cell. Thus, polypeptides or polypeptide monobodies of the present invention which inhibit αvβ3 will be useful as antiviral agents.

As a result of the present invention, polypeptides or polypeptide monobodies of the present invention (with αvβ3 selective binding activity) can be used for blocking αvβ3-mediated events such as cell adhesion, osteoclast-mediated bone resorption, restenosis, ocular neovascularization and growth of hemangiomas, as well as neoplastic cell or tumor growth and dissemination. The inventive polypeptide or polypeptide monobodies can also be used for mediated targeting and delivery of therapeutics for disrupting or killing αvβ3 bearing neoplasms and tumor-related vascular beds. In addition, the inventive polypeptide or polypeptide monobodies can be used for visualization or imaging of αvβ3 bearing neoplasms or tumor related vascular beds, for example, by MRI or immunoscintigraphy.

In addition, these polypeptide or polypeptide monobodies can be used to detect αvβ3 in solution, in frozen tissue sections, and on the surface of cells; therefore, these polypeptides or polypeptide monobodies may be used for the detection and characterization of αvβ3-bearing tumor and endothelial cells in human malignancies. Accordingly, the polypeptides or polypeptide monobodies of the present invention may be used for identification of tumor vasculature. Since the integrin αvβ3 is minimally expressed on resting or normal blood vessels, but is significantly up-regulated on vascular cells within human tumors (Brooks et al., 1994a; Brooks et al., 1994b; Brooks et al., 1995), αvβ3 may be considered a marker of human tumor-associated blood vessels and tumor growth (Brooks et al., 1995). Consequently, polypeptides or polypeptide monobodies that recognize αvβ3 may be used as a diagnostic agent to identify tumor-related blood vessels or vascular beds using conventional immunohistochemical techniques. Further, since the integrin αvβ3 is a marker of tumor-associated blood vessels and recent findings indicate that blood vessel density is a prognostic indicator of cancer and disease status (Weidner, 1993), polypeptides or polypeptide monobodies that recognize αvβ3 may be used as a component of a diagnostic device or technique to measure tumor-related blood vessel abundance or density and to define disease prognosis. Specifically, histologic sections from fresh-frozen or formalin-fixed paraffin embedded tumor tissue are immunostained with αvβ3-specific polypeptides or polypeptide monobodies, i.e., at concentration of 0.1-50 μg/ml, using techniques and procedures known to those skilled in the art. αvβ3-specific polypeptides or polypeptide monobodies bound to vascular endothelial cells in the tissue can be visualized using a polypeptide or polypeptide monobody fusion or a secondary agent that permits localization of the αvβ3-specific polypeptides or polypeptide monobodies bound within the tissue section. For fusions, the αvβ3-specific polypeptides or polypeptide monobodies can be fused with alkaline phosphatase, both of which retain their functionality. The alkaline phosphatase, which is integral with the functional polypeptide or polypeptide monobody portion, can be identified in accordance with known procedures. The secondary agent is typically an antibody that reacts or binds with the αvβ3-specific polypeptides or polypeptide monobodies and has an attached reporter molecule, e.g., an anti-polypeptide or polypeptide monobody antibody with an attached enzyme or fluorescent marker. The polypeptide or polypeptide monobody, when used with secondary agents, is typically provided with an epitope tag fusion, the epitope portion being recognized by the anti-polypeptide or polypeptide monobody antibody. The number and area of immunostained blood vessels in the tissue can then be counted by microscopic techniques, familiar to those skilled in the art, to assess tumor blood vessel density or abundance.

The fusion proteins of the present invention which include a DNA binding polypeptide (e.g., polylysine amino acid sequence) can also be used to deliver a therapeutic DNA molecule into a cell which expresses an integrin targeted by the polypeptide or polypeptide monobody of the present invention, such as the αvβ3 integrin. Polylysine has long been known as a DNA-binding motif because of its role in histone-mediated DNA condensation. This property of polylysine to bind DNA was utilized to deliver the DNA to mammalian cells (Wu & Wu, 1987; Wu & Wu, 1988). The technology was utilized by Zhou et al to develop lipophilic polylysines which were in part the basis of present lipofection delivery of DNA (Zhou et al., 1991). Polylysines conjugated by peptide bond to integrin-binding peptides have been described which effectively deliver DNA to cells (Harbottle et al., 1998). Polylysine DNA has also been used to deliver DNA to endothielial cells, a potential target for αvβ3-selective gene delivery (Trubetskoy et al., 1992). Thus, a fusion protein, as described above, is first combined with the DNA to be delivered under conditions which are effective to allow the DNA binding peptide, such as polylysine, to bind the DNA. Thereafter, the complex formed upon binding of the fusion protein to the DNA, is administered to a patient under conditions effective to deliver the DNA into the cells which express the integrin, e.g., αvβ3, targeted by the fusion protein.

In addition to its administration alone, a number of known delivery techniques can be utilized for the delivery, into cells, of either the polypeptide monobodies themselves or nucleic acid molecules which encode them.

Regardless of the particular method of the present invention which is practiced, when it is desirable to contact a cell (i.e., to be treated) with a polypeptide or polypeptide monobody of the present invention, or its encoding nucleic acid, it is preferred that the contacting be carried out by delivery of the polypeptide monobody or its encoding nucleic acid to the cell.

One approach for delivering the polypeptide or polypeptide monobody to the cell or its encoding nucleic acid into cells involves the use of liposomes. Basically, this involves providing the polypeptide or polypeptide monobody or its encoding nucleic acid to be delivered, and then contacting the target cell with the liposome under conditions effective for delivery of the polypeptide or polypeptide monobody or nucleic acid into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (Wang & Huang, 1987). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al. (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., as well as any other approach demonstrated in the art.

From the foregoing, it should be apparent that the polypeptide or polypeptide monobody can either be delivered in a liposome or, when incorporated into the lipid bilayer(s), used as a means for targeting a liposome to αvβ3 integrin-expressing cells.

An alternative approach for delivery of polypeptide monobodies involves the conjugation of the desired polypeptide or polypeptide monobody to a polymer that is stabilized to avoid enzymatic degradation of the conjugated polypeptide or polypeptide monobody. Conjugated proteins or polypeptides of this type are described in U.S. Pat. No. 5,681,811 to Ekwuribe.

When it is desirable to achieve heterologous expression of a desirable polypeptide or polypeptide monobody of the present invention in a target cell, DNA molecules encoding the polypeptide or polypeptide monobody can be delivered into the cell. Basically, this includes providing a nucleic acid molecule encoding the polypeptide or polypeptide monobody and then introducing the nucleic acid molecule into the cell under conditions effective to express the polypeptide monobody in the cell. Preferably, this is achieved by inserting the nucleic acid molecule into an expression vector before it is introduced into the cell. For intracellular expression in this manner, use of polypeptide monobodies is preferred because such monobodies are enzymatically stable within cells.

When transforming mammalian cells for heterologous expression of a polypeptide or polypeptide monobody of the present invention, an adenovirus vector 5 can be employed. Adenovirus gene delivery vehicles can be readily prepared and utilized given the disclosure provided in Berkner (1988) and Rosenfeld et al. (1991). Adeno-associated viral gene delivery vehicles can be constructed and used to deliver a gene to cells. The use of adeno-associated viral gene delivery vehicles in vivo is described in Flotte et al. (1993) and Kaplitt et al. (1994). Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel.

Retroviral vectors which have been modified to form infective transformation systems can also be used to deliver nucleic acid encoding a desired polypeptide monobody into a target cell. One such type of retroviral vector is disclosed in U.S. Pat. No. 5,849,586 to Kriegler et al.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired polypeptide or polypeptide monobody, allowing the polypeptide or polypeptide monobody to bind to the αvβ3 integrin.

Whether the polypeptides or polypeptide monobodies of the present invention (or encoding nucleic acids) are administered alone or in combination with pharmaceutically or physiologically acceptable carriers, excipients, or stabilizers, or in solid or liquid form such as, tablets, capsules, powders, solutions, suspensions, or emulsions, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. For most therapeutic purposes, the polypeptides or polypeptide monobodies (or encoding nucleic acids) can be administered intravenously.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the polypeptide monobodies or nucleic acids in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Dosages to be administered can be determined according to known procedures, including those which balance both drug efficacy and degree of side effects.

From the foregoing, it should be appreciated that therapeutic methods and compositions are contemplated for inhibiting integrins, particularly $\alpha v \beta 3$ integrin. These methods are useful to inhibit cell attachment and migration mediated by the integrins and find application in a wide variety of cell types, tissues and systems where attachment of cells is not desired. Thus, in general, the invention contemplates a method for inhibiting an integrin that binds a specific ligand by contacting the integrin with an inhibiting amount of an integrin-inhibiting polypeptide or polypeptide monobody (or fusion protein/conjugate containing them) of the present invention. Typically, the method is practiced on cells expressing the integrin on the surface of the cell, so the contacting occurs by exposing the cells to the integrin-inhibiting polypeptides or polypeptide monobodies.

An inhibiting amount of integrin-inhibiting polypeptide or polypeptide monobody is an amount sufficient to produce the desired result, namely to inhibit the integrin to a degree sufficient to reduce the adhesion of the cell expressing the integrin, and typically depends on the amount of integrin to be contacted.

In preferred embodiments, whether the method is practiced in vitro or in vivo, an inhibiting amount is an amount sufficient to provide at least about one molar equivalent of integrin-inhibiting polypeptide or polypeptide monobody per molar equivalent of integrin to be inhibited. This amount is referred to as a stoichiometric amount of integrin-inhibiting polypeptide or polypeptide monobody. Although polypeptide or polypeptide monobody affinity is typically sufficient for an integrin-inhibiting polypeptide or polypeptide monobody to react stoichiometrically in dilute solutions, it is preferred that an inhibiting amount is in the range of about 100 nanomolar (nM) to 1 millimolar (mM), preferably in the range of 1 to 100 micromolar ($\mu$M), more preferably about 1 to 10 $\mu$M.

When an integrin-inhibiting method is practiced in vitro, a liquid sample containing integrin, and preferably a physiological fluid containing cells that express cell surface integrin, are admixed with an inhibiting amount of an integrin-inhibiting polypeptide or polypeptide monobody of the present invention to form a complex. The complex is maintained under biological conditions compatible with the formation of an reaction product and also compatible, if required, with cell viability for a time period sufficient for the integrin-inhibiting polypeptide or polypeptide monobody to react with the integrin and, when reacted, inhibit the integrin.

When the integrin-inhibiting method is practiced in vivo, an inhibiting amount of a polypeptide or polypeptide monobody composition containing a physiologically tolerable diluent and integrin-inhibiting polypeptide or polypeptide monobody molecules as described herein is administered to a mammal, e.g. a human, and the mammal is maintained for a sufficient period to allow the monobody molecules to react with any integrin present and form an inhibiting reaction product. Suitable routes of administration are envisioned as described above, preferably intravenous, intraperitoneal, intra muscular, intrathecal or subcutaneous.

The integrin-inhibiting polypeptide or polypeptide monobody may be combined with other pharmaceutical compositions and/or excipients.

For example, $\alpha v \beta 3$ integrin-inhibiting polypeptide or polypeptide monobody may be co-administered or added to established anti-cancer chemotherapeutic or biotherapeutic regimens. Normal physiologic saline is a preferred excipient or vehicle for administration of the polypeptide or polypeptide monobody. This may include, but is not limited to, combining or co-administering $\alpha v \beta 3$ integrin-inhibiting polypeptide or polypeptide monobody with cytotoxic drugs, combinations of cytotoxic drugs or with immune stimulating drugs, such as interleukins or their derivatives or with hematopoietic factors and their derivatives. For example, $\alpha v \beta 3$ monobody may be co-administered or added to therapeutic regimens for the use IL-1, IL-2, IL-4, IL-6, IL-12, IL-15, TNF, $\alpha$, $\beta$, $\gamma$, interferons and M-CSF, or combinations of these agents or their derivatives, in biologic therapy of cancer. Further, $\alpha v \beta 3$ integrin-inhibiting polypeptide or polypeptide monobody may be co-administered or added to therapeutic regimens for the use of G-CSF, M-CSF, IL-3 and erythropoietin, or combinations of these agents or their derivatives, in biologic therapy of cancer.

In addition to its use alone, the integrin-inhibiting polypeptide or polypeptide monobody may also be conjugated to a chemotherapeutic agent to afford a conjugate that can be administered alone or in combination with other anti-cancer drugs or immune-enhancing drugs of the type described above. Conjugates can be formed using known techniques, although typically the conjugate can be formed by linking the chemotherapeutic agent directly or indirectly, via covalent bond, to the C-terminal or N-terminal regions of the monobody.

For purposes of imaging cancerous or pre-cancerous lesions to assess the degree of angiogenesis and, therefore, the likelihood of metastatic activity, the polypeptide or polypeptide monobody of the present invention can be formed as a fusion protein including a metal ion-complexing polypeptide or formed as a conjugate including a contrasting agent or chelating agent.

Suitable metal ion-complexing polypeptides include, without limitation, polyhistidine. The fusion protein-metal ion complex can be used to identify integrin containing tissues, particularly $\alpha v \beta 3$ integrin containing tissues, i.e., where angiogenesis or neoplasia may be occurring.

The complexation of the metal ions to the fusion protein, and specifically to the metal ion-complexing polypeptide or chelating agent, is achieved by mixing appropriate amounts of the fusion protein with the metal ion. This is preferably done in solution, with the solution including an appropriate buffer. In one approach, the metal ion is, when mixed with the fusion protein, already in the oxidation state required for complexing to the metal ion-complexing polypeptide. Some metal ions are complexed in their most stable oxidation state, such as ionic forms of calcium, potassium, indium, manganese, copper, zinc, cobalt and other metals. In another approach, the metal ions must be reduced to a lower oxidation state in order to be complexed to the metal ion-complexing polypeptide. This is true of ferrous, ferric, stannous, stannic, technetiumoxo[V], pertechnetate, rheniumoxo[V], perrhenate and other similar metal ions. Thus, for example, both perrhenate and pertechnetate must be reduced to a lower oxidation state prior to complexing. Reduction may be performed prior to mixing with the polypeptide, simultaneously with mixing with the fusion protein, or subsequent to mixing with the fusion protein. Any means of reduction of metal ions to the desired oxidation state known to the art may be employed. For example, perrhenate or pertechnetate may be reduced by use of stannous ions, dithionite or other means. The stannous or dithionite metal ion reducing agent may be mixed with the metal ion to be reduced either prior or subsequent to addition of the metal ion to the fusion protein, or the reducing agent may be in solution with the fusion protein when the metal ion to be reduced, and subsequently complexed to the fusion protein, is added to the solution.

The stoichiometric ratios between the fusion protein and the metal ion in the labeling or complexing step can be varied depending on the application. For example, in the case of radiometal complexation, the ratio of radiometal ions to fusion protein molecules can be varied from less than 1:2 to 1:1000 or higher, without generating substantial radiochemical impurities. In other applications, the ratio of metal ions to fusion protein molecules can range from at least 1000:1 to 1:1000 or higher. When the concentration of metal ions is higher than the concentration of fusion protein molecules, all or virtually all of the fusion protein molecules will be complexed to metal ions.

Either radioactive or non-radioactive metal ions can be employed. Where a specific diagnostic or therapeutic advantage can be obtained from use of a radioisotope, then a radioactive metal ion is employed. Where the diagnostic or therapeutic utility is obtained from the conformationally constrained biological-function domain, a non-radioactive metal ion is employed. It is possible and contemplated, and may for certain applications be advantageous, to employ different metal ions with the same conjugate product of this invention.

Suitable contrasting agents include, without limitation, a dextran-coated superparamagnetic iron oxide (SPIO) particle (Reimer et al., 1991; Schaffer et al., 1993; Reimer et al., 1994; Small et al., 1994; Kresse et al., 1998; Suwa et al., 1998), a lipid vesicle or other similar particle with $Gd^{3+}$ attached to the surface (Kabalka et al., 1991; Tilcock et al., 1992; Sipkins et al., 1998), and poly-lysine with $Gd^{3+}$ attached to the amino groups (Kayyem et al., 1995; Vera et al., 1995). Like the fusion proteins containing a metal ion complexing agent, the conjugates containing a contrasting agent can also be used to identify integrin containing tissues, particularly αvβ3 integrin containing tissues, i.e., where angiogenesis or neoplasia may be occurring.

Another type of conjugate includes an organic chelating agent (e.g., diethylenetriamine pentaacetic acid) conjugated to a polypeptide monobody of the present invention which has been modified at, e.g., its C-terminus to include a cysteine residue which will form a stable covalent bond with the chelating agent. Thereafter, the conjugate can be exposed to a suitable metal ion of the type described above in a manner which is effective to allow the conjugated diethylenetriamine pentaacetic acid moiety to complex with the metal ions.

The fusion proteins or conjugates, and the methods of this invention can also be applied to diagnostic agents for use in positron emission tomography (PET) and magnetic resonance imaging (MRI). For use as a PET agent, a fusion protein or conjugate is complexed with one of the various positron emitting metal ions, such as $^{51}Mn$, $^{52}Fe$, $^{60}Cu$, $^{68}Ga$, $^{72}As$, $^{94m}Tc$, $^{110}In$, and isotopes of At. For MRI applications, the complexing metal ion is paramagnetic, such as Mn, Gd, Fe, or Dy.

EXAMPLES

The following Examples are intended to be illustrative and in no way are intended to limit the scope of the present invention.

Materials & Methods

The following materials and methods were used in the experiments set forth in Examples 1-5.

General reagents: All chemicals, unless otherwise specified, were obtained from Sigma (St. Louis, Mo.). Purified integrins, cell adhesion strips, and LM609 were purchased from Chemicon (Temecula, Calif.). Echistatin and GRGD-SPK peptide (SEQ ID No: 26) were obtained from Bachem (Torrence, Calif.).

Cell Culture: K562, K562-αvβ3, K562-αIIbβ3, K562-αvβ5, K562-α4β1, and K562-α4β7 cells were a gift of Dr. S. Blystone (Upstate Medical University, Syracuse, N.Y.) (Blystone et al., 1994). K562 cells were maintained in Iscove's Modified Dulbecco's Medium (IMDM) (Gibco, Invitrogen, Grand Island, N.Y.) supplemented with 10% fetal bovine serum (Sigma), 0.5 U/L penicillin-streptomycin, and 2 mM L-Glutamine (Gibco). K562-αvβ3, K562-αIIbβ3, K562-αvβ5, K562-α4β1, and K562-α4β7 cells were maintained in the same media containing 500 μg/ml G418 (GENETICIN) (Gibco).

Construction of phage vectors: A phage-display vector for FNfn10, designated JCFN, was constructed by cloning the FNfn10 gene (Koide et al., 1998) in the modified M13 vector JC-M13-88 (Chappel et al., 1998). The FNfn10 gene was amplified from pAS38 (Koide et al., 1998) using the following oligonucleotides:

```
FN3JCM8Nhe
                                        (SEQ ID No:29)
cctagctagc gtagctcagg ccatgcaggt ttctgatgtt c   41
and FN3JCM8Hin
                                        (SEQ ID No:30)
ggccaagctt gaccgccacc agaaccgcca ccggtacggt ag  42
``` digested with the restriction enzymes NheI and HindIII, respectively, and subcloned in JC-M13-88 using the same restriction enzyme sites so that the FNfn10 gene is placed in-frame between the OmpA signal sequence and M13 geneVIII. It was confirmed by ELISA that the JCFN phages prepared using E. coli XL-1blue displayed FNfn10 on the phage surface. Purified FNfn10 clones were expressed with an N-terminal histag and a C-terminal GKKGK (SEQ ID No: 31) tag. The GKKGK (SEQ ID No: 31) tag was incorporated to increase the solubility (Koide et al., 1998) and to serve as a preferred biotinylation site. FNfn10 genes were amplified using the following oligonucleotides:

FN1F2

(SEQ ID No:32)

cgggatccca tatgcaggtt tctgatgttc cgcgtgacct ggaagttgtt gctgcgacc 59
and

FN3GKKGK (SEQ ID No:33)

ccgactcgag ttactattta cctttttac cggtacggta gttaatcgag 50 which were digested with the restriction enzymes NdeI and XhoI, and ligated with pAS45 (Koide et al., 1998) digested with the same restriction enzymes. The expression vector for the wild type protein, pAS54, contained an Arg6 to Thr mutation that had been introduced to remove a secondary Thrombin site (Koide et al., 1998).

Construction of the FNfn10 library: A FNfn10 library, JCFN-RGD, was constructed in such a way that the FG loop has an XRGDXXXX sequence where X stands for any amino acids (residue #77-84; residue numbering is according to FIG. 2(a) of Koide et al. (1998)). Mutagenesis on the JCFN template was performed according to Kunkel's method (Kunkel, 1985) using an oligonucleotide, designated JCFN-FGRGD, as follows:

JCFNFGRGD (SEQ ID No: 34)

gttaatcgag attggcttgg arnnnmnnmn mnnatcgccg cgmnnagtaa cagcgtatac 60 where N is a mixture of A, G, C and T, and M is a mixture of A and C). E. coli SS320 was electro-transformed with the mutagenesis mixture, resulting in a phage library containing 1.5×10⁹ independent clones. The phages were re-amplified in E. coli XL1-blue with various concentrations of isopropyl β-D-thiogalactopyranoside (IPTG).

αvβ3 biopanning using the JCFN-RGD library: Integrin biopanning was performed similarly to the method previously described (Koivunen et al., 1994). Purified αvβ3 (5 µg/ml in TBS buffer containing 2 mM CaCl$_2$) was bound to a single microtiter well of a 96-well plate. The well was rinsed 3 times with sterile water containing 2 mM CaCl$_2$ and blocked with 5% phage blocking reagent (Novagen, Darmstadt, Germany) for one hour at room temperature. The plate was rinsed 5 times with TBS buffer containing 0.1% Tween-20 and 2 mM CaCl$_2$, then incubated with JCFN-RGD library diluted in 5% blocking reagent for one hour. The plate was washed ten times with TBS buffer containing 0.1% Tween 20 and 2 mM CaCl$_2$ and bound phage were eluted with 0.2 M glycine-HCl (pH 2.2) containing 1 mg/ml BSA for 10 minutes at room temperature with gentle agitation and neutralized with 15% (v/v) of 1 M Tris-HCl (pH 9.1). The phage were amplified using the E. coli ER2738 host strain (New England Biolabs, Beverly, Mass.) in the presence of 1 mM, 0.1 mM or with no IPTG and purified by precipitating with 20% (w/v) polyethylene glycol-8000, 2.5 M NaCl and resuspending in PBS containing 20% (v/v) glycerol. The biopanning and amplification of eluted phage were repeated for two more rounds. Upon completion of three rounds of biopanning, individual phage clones were amplified and the genomes were purified by phenol extraction. Polymerase chain reaction was performed to amplify the FNfn10 domain using the following primers:

SFN3F (SEQ ID No:35)

agctcaattg gtccggtgga ggttctgatg ttccgcgtga cctg 44
and

SFN3R (SEQ ID No:36)

agctaagctt ttaggtacgg tagttaatcg agat 34

The DNA was also sequenced using the SFN3F primer.

Protein preparation: The expression of FNfn10 proteins was performed as previously described (Koide et al., 1998) except that the proteins were further biotinylated. After biotinylation, the protein-containing solution was applied to a nickel affinity column and unbound materials were washed off; the column was then equilibrated with 50 mM sodium phosphate buffer (pH 8.0) containing 500 mM sodium chloride. D-biotinoyl-ε-aminocaptoic acid N-hydroxysuccinimide ester (726 µM) (Boehringer Mannheim, Mannheim, Germany) in the same buffer was applied to the column, and the column was incubated for an hour at room temperature to perform biotinylation. This biotinylation process was performed a total of three times. Then the column was washed with 20 mM Tris-HCl buffer (pH 8.0) containing 500 mM sodium chloride, and the biotinylated FNfn10 was eluted with the buffer containing 500 mM imidazole. The proteins purified in this manner were >90% pure as judged by SDS-PAGE and reverse phase chromatography. Protein concentrations for subsequent analyses were determined by Bradford assay and confirmed by SDS-PAGE analysis and Coomassie Brilliant Blue staining. Biotinylation was confirmed by Western analysis with streptavidin-horseradish peroxidase (Oncogene, Cambridge, Mass.).

ELISA detection of biotinylated FNfn10 clones: Purified integrin was bound to a flat-bottom, high-binding EIA/RIA plate (Corning Costar, Corning, N.Y.) at a concentration of 5 µg/ml in TBS for 12-16 hours at 4° C. The plate was washed once with TBS and blocked for 2 hours at room temperature with 0.1M NaHCO$_3$, 0.5 mg/ml BSA, 0.2% NaN$_3$, pH 8.6. Biotinylated FNfn10 clones were bound in TBST+Ca$^{2+}$ (TBS 0.1% Tween-20, 2 mM CaCl$_2$). Plates were washed ten times with TBST+Ca$^{2+}$ and incubated 20 minutes with 2 µg/ml streptavidin-horseradish peroxidase (Oncogene) in TBST+Ca$^{2+}$ at room temperature. Plates were washed ten times with TBST+Ca$^{2+}$. Bound peroxidase was detected with ABTS (2,2'-azino-di-3-ethyl-benzthiazoline sulfonic acid) peroxidase substrate (Sigma), 1 mg/ml in 0.1 M NaCitrate, 0.1 M Na$_2$HPO4, pH 4.0 supplemented with 0.03% hydrogen per-oxide. Color was allowed to develop for 10-15 minutes and the $A_{400}$ was read with a SpectraCount ELISA reader (Packard, Downers Grove, Ill.).

Flow cytometric detection of cell-binding by biotinylated FNfn10 & FNfn10-3JCLI4: K562 cells ($10^5$) transfected with various integrins were resuspended in 5 ml FACS buffer (PBS, 0.5% BSA, 0.1% $NaN_3$), washed, and resuspended in FACS buffer containing either 0.4 µg/ml FNfn10 protein (wild-type of 3JCLI4) or 1 µg/ml LM609, prior to incubation at room temperature for 20 minutes. Cells were then washed with 5 ml FACS buffer, incubated in 1:50 streptavidin-APC (BD Pharmingen, San Diego, Calif.) for 20 minutes and washed again with 5 ml FACS buffer, prior to detection of cell surface fluorescence using a FACSCalibur flow cytometer (Becton Dickinson, San Jose, Calif.).

Cell adhesion assays: Fibronectin and vitronectin-coated strips (Chemicon) were rehydrated 15 minutes in PBS. Inhibitor in IMDM/10% FBS was added to the bottom of the well, and $10^5$ cells/well in maintenance media were added to a final volume of 100 µl/well. Cells were incubated 2 hrs at 37° C., 5% $CO_2$, washed three times with PBS at room temperature, and stained 10 minutes with 0.2% crystal violet, 10% ethanol. Cells were then washed three times with PBS and solubilized with a 1:1 ratio of PBS:absolute ethanol for 10 minutes with agitation. $A_{600}$ was measured using a Spectra-Count ELISA reader (Packard).

Example 1

Screening of the JCFN-RGD Phage Display Library for αvβ3 Integrin Binding

In the FNfn10 structure of SEQ ID No: 2 (wild-type), the FG loop corresponds to residues 78-87, and the RGD sequence to residues 79-81 (residue numbering according to the Protein Data Bank entry 1TTG, Main et al., 1992). Five residues immediately adjacent to the RGD sequence were modified in the FG loop using Kunkel mutagenesis as described above. The JCFN-RGD (XRGDXXXX, SEQ ID No: 4) library contained 1.5×$10^9$ independent clones, sufficiently large to include all possible sequences. The library was amplified in 0.0, 0.1, or 1.0 mM IPTG to vary FNfn10 copy number and screened for binding to αvβ3 integrin. After 3 rounds of biopanning, 100-1000 fold increased recovery of phage was observed compared to the initial library. Of 20 phage clones sequenced, 8 contained an XRGDWXEX (SEQ ID No: 26) consensus sequence (FIG. 4A). Phage inputs of $10^9$, $10^8$, or $10^7$ pfu were then allowed to bind to αvβ3 or BSA coated wells and bound phages were recovered with 0.2M glycine, pH 2.2. Using phage clones amplified in 1 mM IPTG (high FNfn10 copy number), phage clones containing the consensus were recovered at levels of 0.01-1% input from αvβ3 coated wells; the clones were recovered at approximately 1000-fold lower levels from BSA coated wells and integrin-binding was found to be calcium-dependent. In contrast, clones which lacked the XRGDWXEX (SEQ ID No: 26) motif were recovered at equivalent levels from both αvβ3 coated and BSA coated wells.

The RGDWXE-containing clones were amplified in the absence of IPTG so as to decrease the expressed copy number of FNfn10 protein on the phage surface, and the panel of clones were then directly compared in a phage binding assay, for their ability to bind to αvβ3 (FIG. 4B). The clones recovered at the highest level were 2JCAV1, 2JCAV2, 3JCAV3, 3JCNI1, and 3JCLI4, all of which were recovered at a level of approximately 0.1% of input phage from αvβ3-coated wells and at 1000-fold lower levels from BSA-coated wells. Therefore, varying FNfn10 copy number on M13 by IPTG concentration did not have an effect on the relative binding efficiency of the clones isolated, suggesting that the binding interaction between the αvβ3 integrin and the phage-displayed FNfn10 derivatives might be of high affinity.

The modified FNfn10 proteins expressed by this panel of phage clones were expressed as an isolated protein in *E. coli*, purified and biotinylated. 3JCLI4 (the second-highest recovered clone in phage binding assays), was selected for further study because the purified FNfn10 protein derived from clone 2JCAV1 (the highest recovered clone) proved to be rather insoluble and prone to precipitation. SDS polyacrylamide gel electrophoresis and Coomassie blue staining revealed the presence of a single protein of the expected size (~15 kDa) within the purified preparation of biotinylated FNfn10-3JCLI4 protein. Western blot analysis using a monoclonal antibody specific for the hexahistidine epitope tag on the purified FNfn10 protein confirmed the identity of this protein, and further analysis revealed that the binding of both the phage clone 3JCLI4 and of the corresponding purified protein (FNfn10-3JCLI4) to αvβ3 integrin was $Ca^{++}$ dependent and could be eliminated in the presence of EDTA.

Example 2

Determining Affinity and Specificity of FNfn10-3JCLI4 for αvβ3 Integrin

Figure 5A:
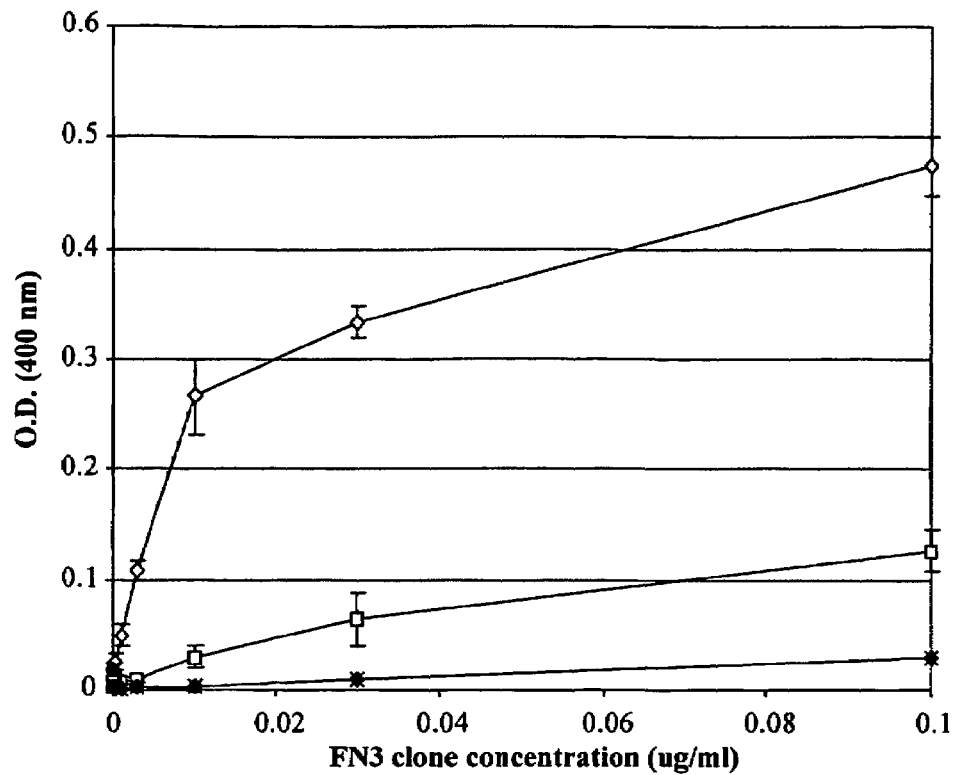
FIGS. 5A-D are graphs illustrating the assessment of FNfn10-3JCLI4 binding affinity to αvβ3 integrin by ELISA. To determine the half-maximal binding concentration of biotinylated FNfn10-3JCLI4 versus biotinylated FNfn10-WT, wells of a 96-well plate were coated αvβ3 (5 μg/ml), α1β1 (5 μg/ml), or BSA (0.5 mg/ml) and blocked with BSA (FIG. 5A). Biotinylated FNfn10-3JCLI4 and FNfn10-WT were then added to the wells and allowed to bind for two hours. Bound protein was detected by streptavidin-horseradish peroxidase (2 μg/ml) and ABTS substrate. $O.D._{400}$ measurements were recorded for biotinylated FNfn10-3JCLI4 binding to αvβ3 (◇), to α1β1 (◆), or to BSA (X) and biotinylated FNfn10-WT binding to αvβ3 (□). Error bars reflect the standard deviation between triplicate wells. To examine protein dissociation over a prolonged (24 hour) time period, a 96-well plate was coated with 5 μg/ml αvβ3 integrin and then incubated with 0.02 μg/ml biotinylated FNfn10-3JCLI4 for two hours; as a control, 10 mM EDTA was added to certain wells, in order to calculate the background level of FNfn10-3JCLI4 binding (FIG. 5B). After rinsing, 2 μg/ml unlabelled FNfn10-3JCLI4 was added to the preformed protein complexes present in the wells 24, 14, 4, 2 and 1 hours prior to detection of remaining plate-bound biotinylated FNfn10-3JCLI4 using streptavidin-horseradish peroxidase and ABTS. Baseline binding activity (100%) was calculated as the amount of biotinylated FNfn10-3JCLI4 which remained bound to the plate following incubation of the well for 24 hours, in the presence of buffer alone (i.e., in the absence of any competitor protein), and the $O.D._{400}$ of FNfn10-3JCLI4 bound in the presence of 10 mM EDTA was subtracted as background. All incubations with competitor (background-subtracted) are expressed as a percentage of the $O.D._{400}$ of baseline binding (background-subtracted). Error bars reflect the standard deviation between triplicate wells. To examine the rate of association of αvβ3 and biotinylated FNfn10-3JCLI4, a 96-well plate coated with 5 μg/ml αvβ3 integrin was blocked with BSA (FIG. 5C). 0.01 (▲), 0.02 (■), or 0.05 (◆) μg/ml of biotinylated FNfn10-3JCLI4 was then added to the coated wells, at 240, 30, 10, 3, and 1 minute prior to washing and detection. After detection with streptavidin-horseradish peroxidase/ABTS, the $O.D._{400}$ of the plate was recorded. Error bars reflect the standard deviation between triplicate wells. A 96-well plate was coated with αvβ3, αvβ5, αIIbβ3, α1β1, and α5β1 purified integrins, all at 5 μg/ml (FIG. 5D). Biotinylated FNfn10-3JCLI4 (dark bars) or FNfn10-WT (light bars) was then added at a concentration of 0.01 μg/ml, and allowed to incubate for 2 hours, followed by washing and detection. Error bars reflect the standard deviation between triplicate wells.

Biotinylated FNfn10-3JCLI4 and biotinylated wild-type FNfn10 (FNfn10-WT) were allowed to bind to αvβ3, α1β1, or BSA coated wells in approximate half-log increments from 0.0001 to 0.1 µg/ml, corresponding to molar concentrations of 8 pM to 8 nM. Bound biotinylated protein was detected by ELISA (FIG. 5A). Assuming a high ratio of free to bound FNfn10-3JCLI4, the equation $y=(m_1*x/(m_2+x))$ was fit to the data (R>0.99) to determine the half-maximal binding affinity of 0.01 µg/ml or 800 pM. At each concentration examined, the binding of biotinylated FNfn10-3JCLI4 to αvβ3 was higher than that for FNfn10-WT, and neither protein was found to bind detectably to the α1β1 integrin (i.e., binding to α1β1 was identical to binding to BSA).

Figure 5B:
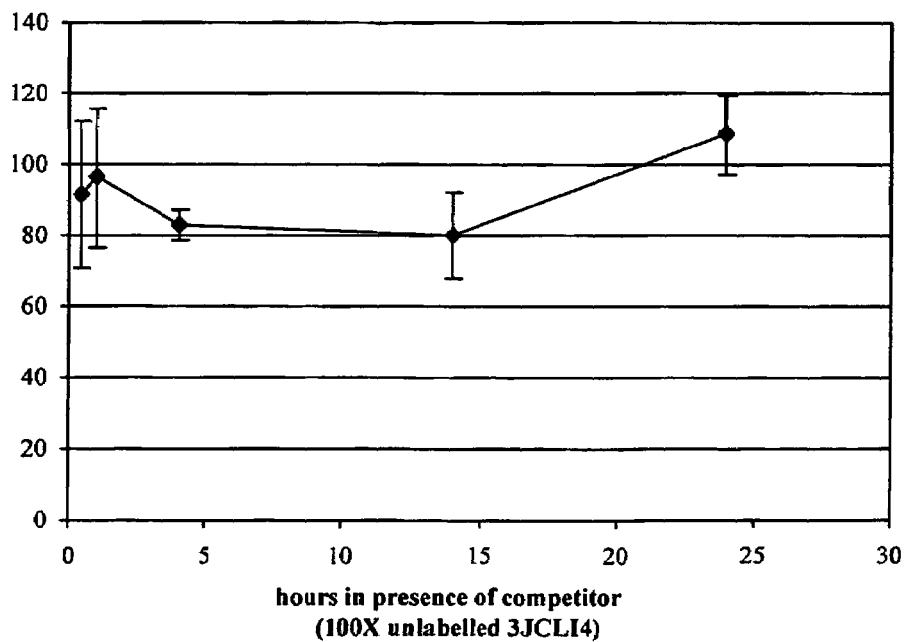

Next, the kinetics of protein association and dissociation was examined. After allowing biotinylated FNfn10-3JCLI4 to bind to αvβ3-coated wells, 100 fold excess unlabelled FNfn10-3JCLI4 was added to some wells and the plates were incubated for a further 24 hours; control wells received were incubated in the absence of the unlabelled competitor. At the end of this time, the amount of plate-bound biotinylated FNfn10-3JCLI4 was assessed by ELISA assay. No difference was detected between wells that were incubated for 24 hours in the presence or absence of excess unlabelled competitor protein. This suggests that the rate of dissociation of FNfn10-3JCLI4 from αvβ3 is very slow (>24 hours; FIG. 5B).

Figure 5C:
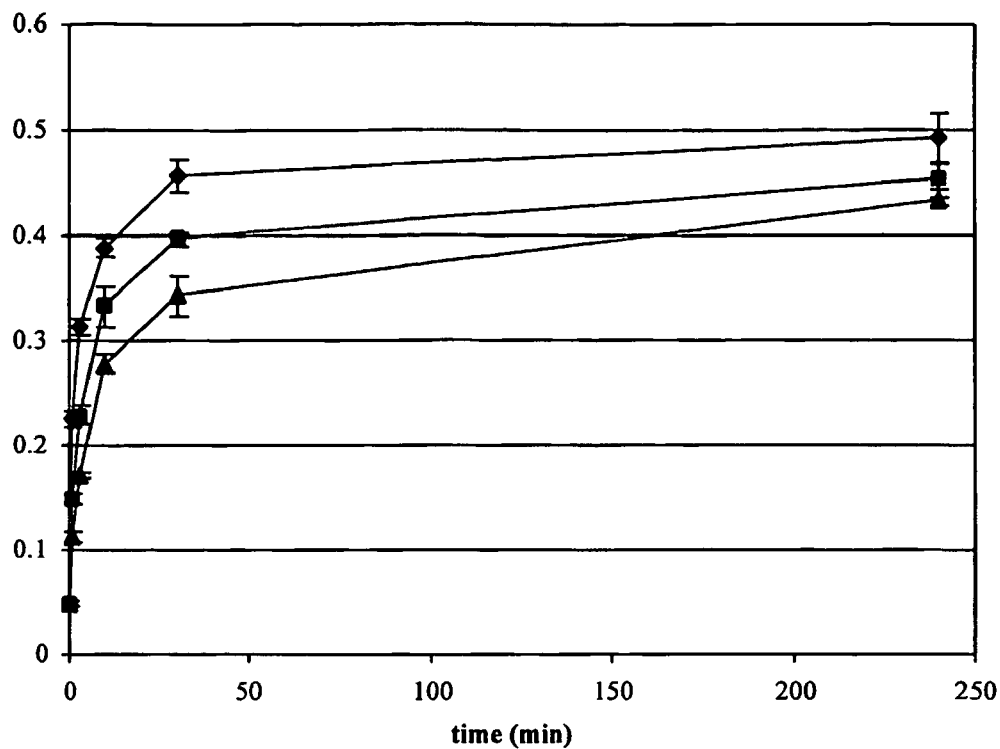
Figure 5D:
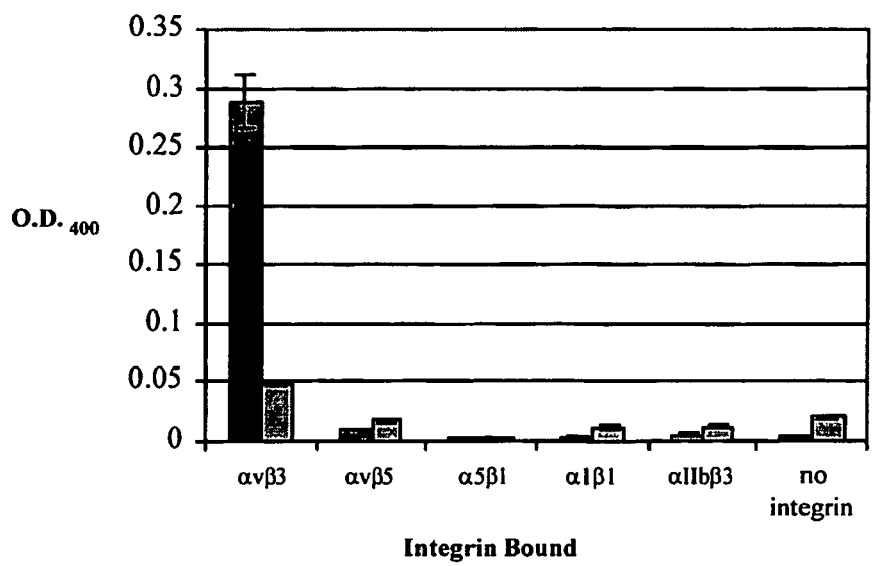

To examine the rate of association between αvβ3 and biotinylated 3JCLI4, biotinylated FNfn10-3JCLI4, at concentrations of 0.01, 0.02, or 0.05 µg/ml, was allowed to bind to αvβ3-coated wells for periods of time ranging from one minute to two hours. For all three concentrations, levels of bound FNfn10-3JCLI4 were detectable within one minute and reached saturation levels within two hours (FIG. 5C). Therefore, in light of the prolonged dissociation rate revealed in FIG. 5B, it can be inferred that FNfn10-3JLCI4 possesses a relatively rapid on-rate for binding to αvβ3.

To test the specificity of the interaction between FNfn10-3JCLI4 and αvβ3 integrin, biotinylated FNfn10-3JCLI4 or FNfn10-WT were added to wells coated with equivalent 5 µg/ml concentrations of different purified integrins (FIG.

5D). In this assay, the detection of plate-bound FNfn10-3JCLI4 was significant only for those wells which had been coated with αvβ3, and not for wells coated with other integrins, including αvβ5, α5β1, α1β1 and αIIbβ3.

Example 3

Determining Relative Affinity of FNfn10-3JCLI4 for αvβ3 Integrin

Figure 6A:
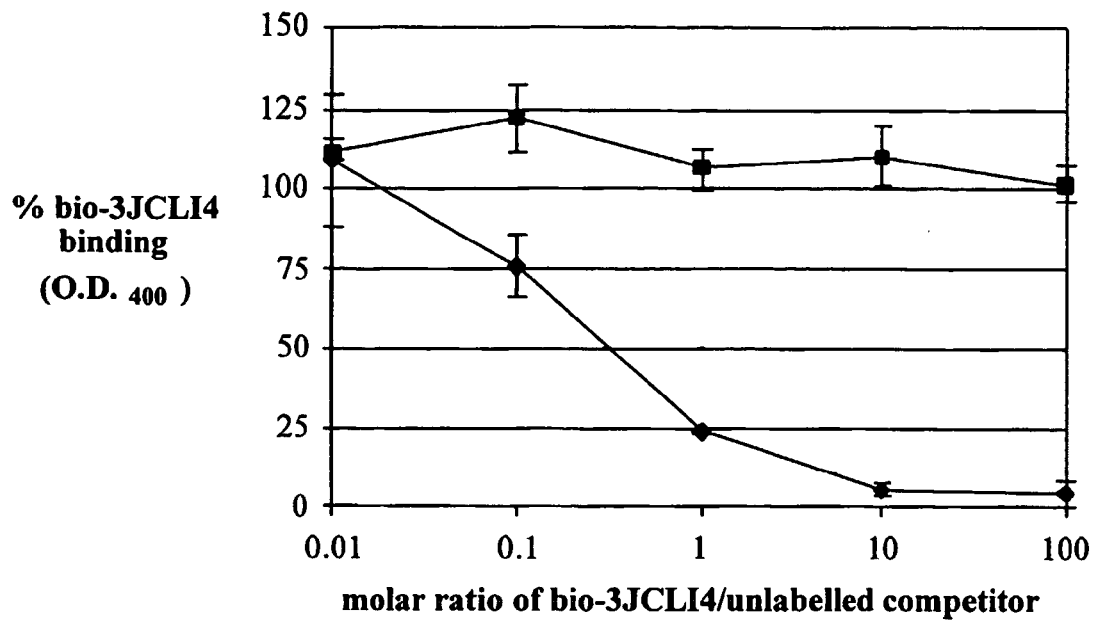
FIGS. 6A-B are graphs illustrating competition ELISAs to determine relative affinities of FNfn10-3JCLI4, echistatin, FNfn10-WT, and GRGDSPK peptide (SEQ ID No: 27). A BSA-blocked 96-well plate which was coated with αvβ3 at 5 μg/ml, after which biotinylated FNfn10-3JCLI4 was then added in the presence or absence of a 0.01, 0.1, 1, 10, or 100-fold molar excess of unlabelled competitor protein, and incubated for two hours. After washing and detection, the $O.D._{400}$ of the plate was recorded. Error bars reflect the standard deviation between triplicate wells, and the results shown are representative of three different experiments that yielded similar results. A background subtraction was performed on all data points, by subtracting the measured $O.D._{400}$ value that corresponded to binding of biotinylated FNfn10-3JCLI4 in the presence of 10 mM EDTA. All values in the figure are expressed as a percentage of the $O.D._{400}$ of biotinylated FNfn10-3JCLI4 binding in the absence of competitor.
Figure 6B:
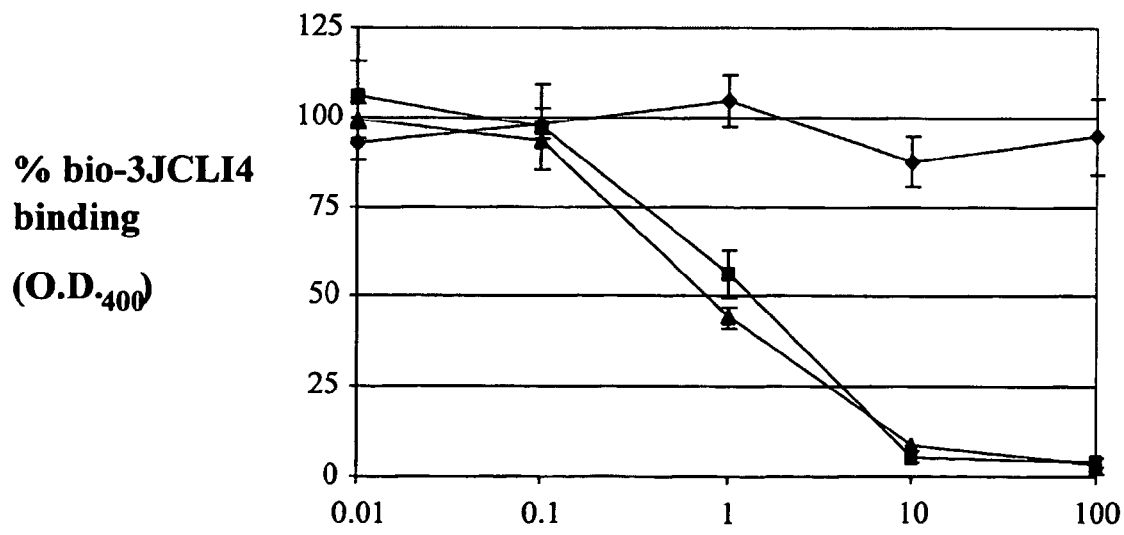

In order to examine the relative affinity of FNfn10-3JCLI4, as compared to other αvβ3 binding molecules, a competition ELISA analysis was performed. In these experiments, biotinylated FNfn10-3JCLI4 at 800 pM was mixed with molar ratios of competitor proteins ranging from 0.01 to 100, and allowed to bind to αvβ3 coated wells (FIGS. 6A and 6B). Binding of biotinylated FNfn10-3JCLI4 to αvβ3 was unaffected by the presence of the linear integrin-binding peptide (GRGDSPK, SEQ ID No: 27) or FNfn10-WT, even when these molecules were added at 100-fold molar excess (80 nM), relative to FNfn10-3JCLI4. In contrast, unlabelled FNfn10-3JCLI4 and echistatin inhibited binding of biotinylated FNfn10-3JCLI4 at roughly equal equimolar concentrations ($IC_{50}$ values were 750 and 930 pM, respectively, as calculated by logarithmic curve-fit). These findings strongly suggest that FNfn10-3JCLI4 and echistatin have roughly equivalent affinities for αvβ3. Echistatin has a published Kd of 330 pM (Kumar et al., 1997).

Example 4

Role of FNfn10-3JCLI4 as a Staining Agent for αvβ3 Integrin

Figure 7A:
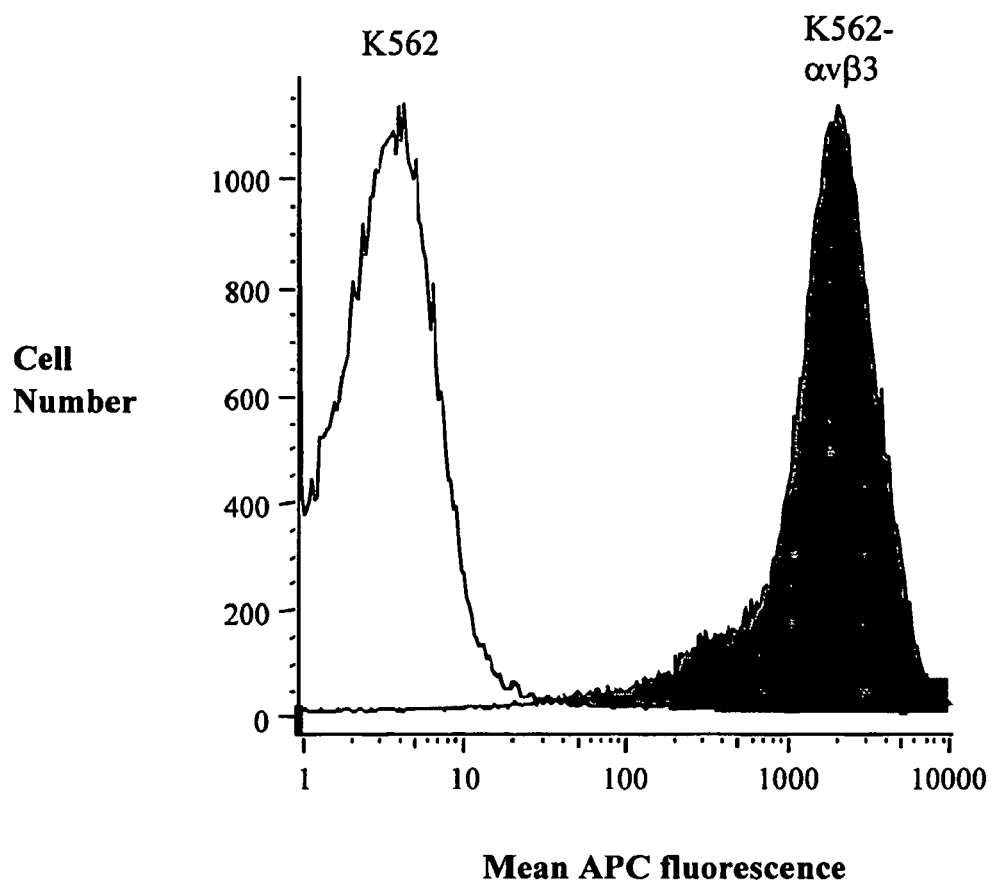
FIGS. 7A-C are graphs illustrating fluorescence activated cell sorting (FACS) analysis of FNfn10-3JCLI4 binding to human cells. Biotinylated FNfn10-3JCLI4 or FNfn10-WT were added to $10^5$ cells at a concentration of 1 μg/ml and incubated for 30 minutes. Bound proteins were then detected with streptavidin-APC, and the mean fluorescence of ten thousand cells per sample was recorded. All experiments were performed three times, with similar results; error bars (FIGS. 7B-C) represent the standard deviation of three samples of 105 cells stained separately.

Biotinylated FNfn10-3JCLI4 (1 µg/ml) was added to wild-type K562 cells and to K562 cells that had been stably transfected with αvβ3 integrin (generous gift of Dr. S. Blystone). Surface bound FNfn10-3JCLI4 was then detected using streptavidin-APC and stained cells were enumerated by flow cytometry. The mean fluorescence intensity of staining on the αvβ3-positive cells was approximately three logs higher than on the non-transfected control cells (FIG. 7A), and concentrations of biotinylated FNfn10-3JCLI4 as low as 0.008 µg/ml were found to be capable of effectively and specifically staining K562-αvβ3 cells.

Figure 7B:
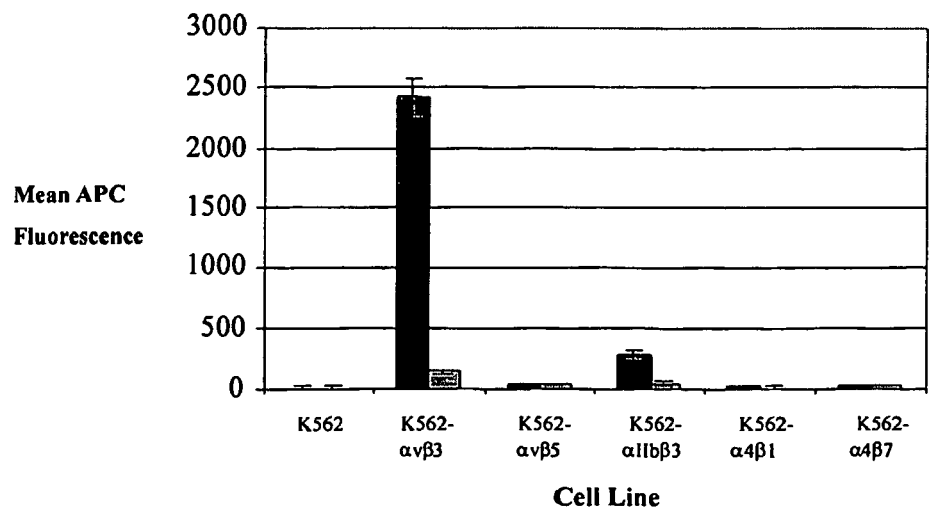

Having optimized the staining analysis using the K562-αvβ3 cells, a more complete analysis of the specificity of cell surface binding of biotinylated FNfn10-3JCLI4 was performed, using a panel of K562 cell sublines, each of which had been stably transfected with various integrin heterodimers (αvβ3, αvβ5, αIIbβ3, α4β1, and α4β7; all gifts of S. Blystone) (Blystone et al., 1994). These experiments revealed that FNfn10-3JCLI4 showed a strong selective preference for αvβ3, although it did also react very weakly with αIIbβ3 positive cells. In contrast, FNfn10-WT showed a slight preference for cells expressing αvβ3, but stained all of the K562 lines with low intensity (FIG. 7B).

Figure 7C:
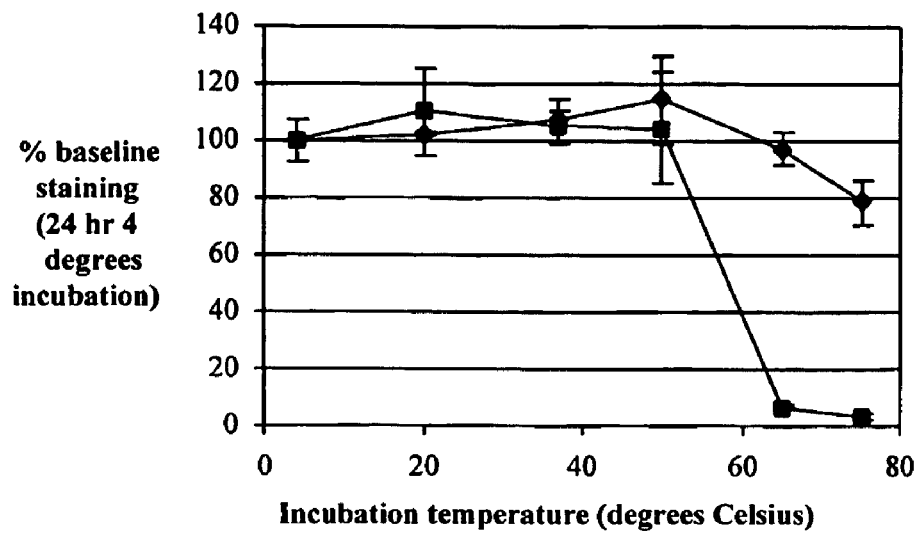

One of the unique properties of the FNfn10 scaffold is its high level of physical stability. Therefore, an examination was performed to determine the effect of prolonged incubation at elevated temperatures on the binding activity of FNfn10-3JCLI4, as compared to the αvβ3s-specific monoclonal antibody, LM609. In these studies, FNfn10-3JCLI4 and LM609 were incubated for 24 hours at 4, 20, 37, 50, 65, or 75 degrees Celsius, prior to addition to K562-αvβ3 cells and performance of flow cytometry. As can be observed in FIG. 7C, incubation of FNfn10-3JCLI4 at 75° C. for 24 hours had only a modest effect on its cell binding activity; in contrast, the same conditions resulted in the complete elimination of LM609's ability to interact with αvβ3.

Example 5

Role of FNfn10-3JCLI4 as an Inhibitor of αvβ3-Dependent Cell Adhesion

K562-αvβ3 cells, but not K562 cells, adhere strongly to vitronectin (but not BSA). This property was therefore used as the basis for a quantitative assessment of the ability of FNfn10-3JLCI4 to disrupt αvβ3 dependent cell adhesion. To do this, K562-αvβ3 cells were allowed to adhere to vitronectin-coated wells, and the number of bound cells per well was then quantified by crystal violet staining and cell solubilization.

Figure 8A:
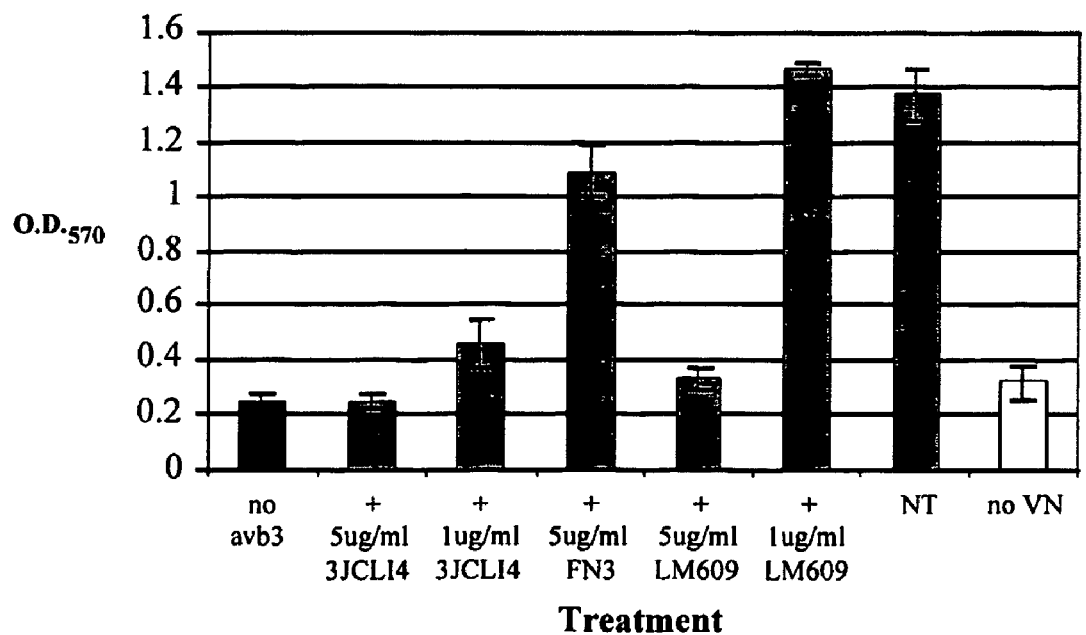
FIGS. 8A-C illustrate the inhibition of integrin-dependent cell adhesion. Vitronectin (FIGS. 8A-B) or fibronectin (FIG. 8C), as well as BSA-coated control wells, were incubated with 10⁵ K562 cells, K562-αvβ3 cells, or K562-αIIbβ3 cells for two hours in the presence or absence of the indicated inhibitors. Non-adherent cells were removed by washing, while adherent cells were stained with crystal violet, solubilized, and quantitated by measuring the O.D.$_{570}$. The background level of crystal violet in control wells was calculated on the basis of measured O.D.$_{570}$ for BSA-coated wells (no integrin). Error bars represent the standard deviation of triplicate wells, and all experiments were performed three times, with similar results.
Figure 8B:
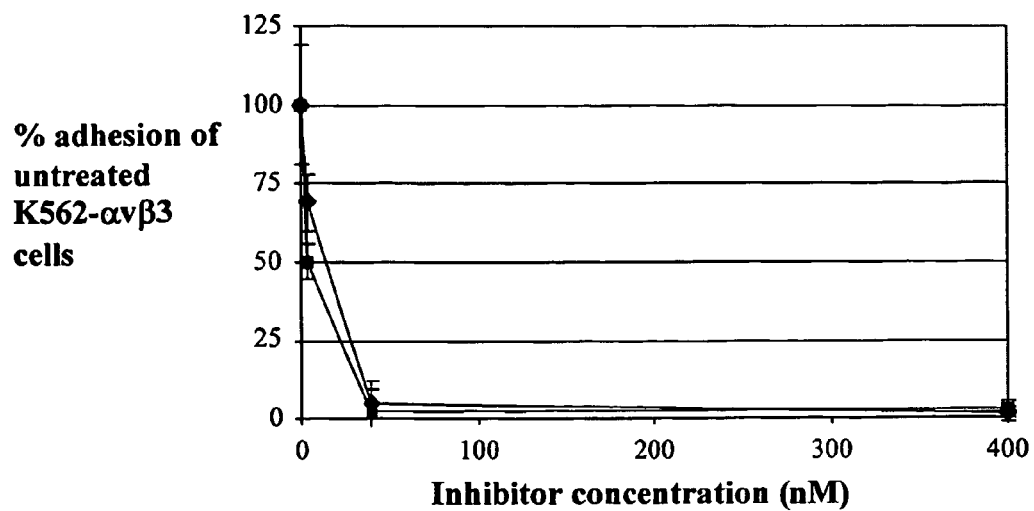
Figure 8C:
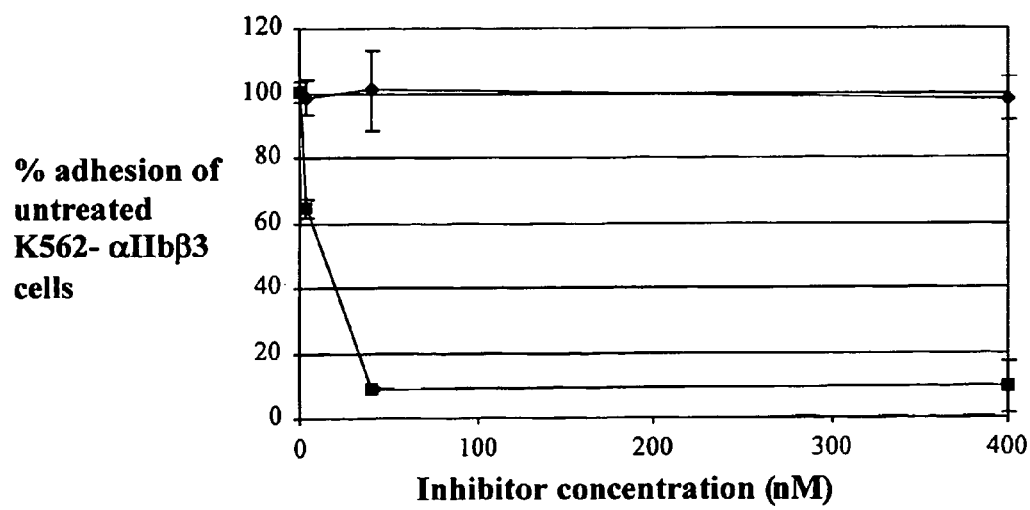

LM609, a commonly used αvβ3 function-blocking antibody, and FNfn10-3JCLI4 were both found to inhibit adhesion of K562-αvβ3 cells to vitronectin, while FNfn10-WT showed little effect in this assay (FIG. 8A). A more careful analysis, using a wider range of protein concentrations, revealed that FNfn10-3JCLI4 inhibits αvβ3-dependent adhesion to vitronectin at approximately the same concentrations as the well-characterized αvβ3-binding disintegrin, echistatin (FIG. 8B). Based on an exponential curve-fit, echistatin was found to inhibit αvβ3-mediated cell adhesion to vitronectin with an $IC_{50}$ of 5.9 nM, while FNfn10-3JCLI4 inhibited αvβ3-dependent adhesion to vitronectin with an $IC_{50}$ of 8.6 nM (R>0.99 in both cases). Finally, the effect of FNfn10-3JCLI4 on αIIbβ3-dependent cell adhesion was also examined, because of the weak binding activity of FNfn10-3JCLI4 for K562-αIIbβ3 cells that was revealed in the flow cytometric analyses (Example 4 above). These experiments revealed that FNfn10-3JCLI4 had no measurable effect on αIIbβ3-mediated cell adhesion to fibronectin, while echistatin inhibited αIIbβ3-dependent adhesion with an $IC_{50}$ of 10.2 nM (R>0.99; FIG. 8C).

Discussion of Examples 1-5

In this work, phage display technology and random mutagenesis techniques were applied to carry out affinity maturation of FNfn10 binding to αvβ3 integrin. Using one phage clone that was derived from a biopanning screen against immobilized αvβ3, 3JCLI4, the following was observed: (i) modified FNfn10 phage clones, including 3JCLI4, which bind to αvβ3 integrin all contain an XRGD-WXEX (SEQ ID No: 26) consensus and exhibit calcium-dependent binding; (ii) purified FNfn10-3JCLI4 protein binds to immobilized human αvβ3 integrin with much higher affinity than FNfn10-WT and exhibits only background binding to other purified integrins; (iii) binding of FNfn10-3JLCI4 to αvβ3 could be successfully competed using approximately equimolar concentrations of unlabelled FNfn10-3JCLI4 or echistatin, but not by either FNfn10-WT or GRGDSPK peptide (SEQ ID No: 27), even when added at 100-fold molar excess, (iv) FNfn10-3JCLI4 is a sensitive and specific reagent for the detection of human αvβ3 integrin in flow cytometry applications; (v) the binding of FNfn10-3JCLI4 to αvβ3 integrin is maintained even after prolonged exposure of FNfn10-3JCLI4 to high temperature, and (vi) FNfn10-3JCLI4 inhibits cell adhesion via αvβ3 but not αIIbβ3 integrin at nanomolar concentrations.

The RGDW sequence that was detected in the αvβ3-selected FNfn10-display phage clones has previously been reported to be preferentially selective for αIIbβ3 integrin over αvβ3, at least in the context of disintegrins such as eristostatin (McLane et al., 1996). RGDW peptides are also used to induce integrin activation and in competition assays with putative αIIbβ3 integrin ligands (Hantgan et al., 1992). Therefore, it was quite unexpected that the consensus sequence (XRGDWXEX, SEQ ID No: 26) bound preferentially to αvβ3 over αIIbβ3 integrins.

Because FNfn10-3JCLI4 exhibits no binding to plate-immobilized αIIbβ3 and very low cross-reactivity with αIIbβ3-positive cells in flow cytometric analysis, the tertiary structure of FNfn10 may play a role in the increased specificity of this RGDW-containing molecule for αvβ3 integrin. Alternatively, the glutamic acid residue within the extended consensus motif (SEQ ID No: 26) may be significant. The disintegrins eristostatin and EC6B each contain an aspartic acid residue at the corresponding location (RGDWN<u>D</u>, SEQ ID No: 28) (McLane et al., 1996; Scarborough et al., 1993; Marcinkiewicz et al., 2000), and though they both bind αvβ3, they interact preferentially with αIIbβ3.

Like the disintegrins, FNfn10-3JCLI4 is a small monomeric molecule with high integrin-binding affinity. In the above Examples, echistatin and FNfn10-3JCLI4 were inferred to have similar binding affinities for αvβ3 because they were both able to compete with biotinylated FNfn10-3JCLI4 for binding to immobilized αvβ3, at roughly equimolar concentrations. Consistent with this, echistatin has a reported $K_d$ of 330 pM for αvβ3 (Kumar et al., 1997), while the value calculated here for the half-maximal binding affinity of FNfn10-3JCLI4 for αvβ3 was 800 pM.

Biochemical analyses revealed a rapid rate of association rate between FNfn10-3JCLI4 and αvβ3 (minutes), and a very slow rate of dissociation (>24 hours). These properties, combined with its high affinity for αvβ3, suggested that FNfn10-3JCLI4 might be suitable for use in flow cytometric applications. Experimental analysis revealed this was indeed the case, and these studies also showed that FNfn10-3JCLI4 performed similarly to αvβ3-specific monoclonal antibodies in flow cytometric staining using K562-αvβ3 cells. It should be noted that FNfn10-3JCLI4 is monomeric, unlike monoclonal antibodies (divalent) or other cell-staining reagents used in flow cytometry (MHC:peptide tetramers). Furthermore, FNfn10-3JCLI4 is considerably more stable than a typical monoclonal antibody, as revealed by its ability to continue to bind αvβ3, even after 24 hr. incubation at 75° C.

A problem encountered in many molecules that target αvβ3 integrins is their cross-reactivity with other integrin subtypes, particularly other αv or β3 integrins. FNfn10-3JCLI4 was found to bind only to immobilized purified αvβ3, and not to other integrins tested. The failure of FNfn10-WT and FNfn10-3JCLI4 to interact with α5β1 is consistent with previous reports that the ninth and eighth fibronectin type III domains are also required for FNfn10 binding to α5β1 (Altroff et al., 2001). In addition, the inability of FNfn10-3JCLI4 to bind to αvβ5 and αIIbβ3, suggests that its integrin-binding activity is likely dependent on a structural interaction with the αvβ3 complex and not with either subunit alone. The narrow integrin-binding specificity of FNfn10-3JCLI4 can be contrasted with the more broad integrin-binding profile that is exhibited by disintegrins such as eristostatin and kistrin, which bind to both αIIbβ3 and αvβ3 (McLane et al., 1996). Similarly, the penton base protein from adenovirus type 5 binds to both αvβ3 and αvβ5, and even an engineered Fab construct (WOW-1) has been shown to exhibit cross-reactivity with αvβ5 integrin (Pampori et al., 1999).

Although FNfn10-3JCLI4 did exhibit a weak interaction with αIIbβ3 in the flow cytometry assay, this will not be a major detriment to the more widespread use of this molecule in cell staining applications because (i) no interaction with αIIbβ3 was detected in biochemical binding studies, (ii) binding to αIIbβ3 positive cells was almost 10-fold weaker than binding to αvβ3-positive cells in the flow cytometric analysis, and (iii) αIIbβ3 expression is limited to platelets. The ability of FNfn10-3JCLI4 to block αvβ3-dependent cell adhesion but not αIIbβ3-mediated cell binding further supports its specificity for αvβ3.

The structure of FNfn10-3JCLI4 is advantageous for multiple applications; FNfn10-3JCLI4 lacks disulfide bonds rendering it resistant against reducing agents, is very stable even at high temperature, and can be produced in a bacterial expression system with yields of up to 50-100 mg per liter of culture. As an endogenous human protein, wild-type fibronectin does not elicit an immune response and it is anticipated that FNfn10-3JCLI4 is likely to be similarly non-immunogenic. Furthermore, because FNfn10-3JCLI4 is a monomer that lacks disulfide bonds, it has several advantages over a monoclonal antibody with similar affinity. As a small, single-chain molecule, FNfn10-3JCLI4 could potentially be incorporated into gene delivery vectors (e.g. viral vectors, liposomes) for cell or tissue-specific gene expression. Indeed, the incorporation of low-affinity RGD peptides into various viral vectors, and the addition of bispecific antibody complexes to viral surface components, have already been shown to result in desirable improvements in vector specificity and transduction efficiency (Haisma et al., 2000; Wickham et al., 1996; Wickham et al., 1997; Hart, 1999). αvβ3-positive cells that may be of particular interest for targeted vector systems include dendritic cells (for vaccine applications) as well as osteoclasts and angiogenic vessels. Finally, FNfn10-3JCLI4 will likely have utility as a cancer imaging agent, because of its ability to recognize αvβ3 on tumor vasculature.

Example 6

Formation of αvβ3-directed MRI Diagnostic with Superparamagnetic Iron Oxide Particles Polypeptide monobodies prepared as described in Example 1 will be used to form an MRI diagnostic agent upon conjugation to superparamagnetic iron oxide (SPIO) particles. Dextran-coated SPIO particles can be purchased (Advanced Magnetics, Cambridge, Mass.) or synthesized as described previously (Kresse et al., 1998). SPIO particles are extremely effective relaxation agents, especially as effectors of $T2^*$. The half-life of SPIO particles in blood highly depends on particle size (Moore et al., 2000) and will be an important factor in the design. A long half-life is useful for allowing time for the contrast agent to escape the capillaries and penetrate into tissue. However, αvβ3 is highly accessible to intravascular compounds, and a long blood half-life increases a background, non-specific signal enhancement. Therefore, SPIO particles with diameter >30 nm that have short blood half-lives of 8-20 minutes (Reimer et al., 1992; Moore et al., 2000) will be used. This should allow sufficient time for binding to αvβ3 and an acceptably short time for clearance of unbound agent. Particle size is primarily determined by the amount of dextran used during oxide crystal precipitation. Size distribution will be determined by a dynamic light scattering instrumentation according to known procedures.

Conjugation between the polypeptide monobody and SPIO will be achieved using a streptavidin-biotin linkage. Two approaches will be employed.

In a first approach, a fusion protein will be expressed from a chimeric gene which includes a polypeptide monobody coding region and streptavidin-biotin coding region linked by an in-frame gene fusion. The chimeric gene will be inserted into an *E. coli* expression vector (pET derivative) to produce a biotinylated protein.

In a second approach, a polypeptide monobody will be expressed containing a free cysteine in the C-terminal flexible tail. Thereafter, the polypeptide monobody will be biotinylated by chemical modification. Unlike antibodies and cyclic peptides, FN3 have no cysteine residues that would complicate cysteine modification. These proteins also contain a poly-histidine tag in the C-terminal tail for purification. The C-terminus of FN3 is located at the opposite side of the protein from the RGD sequence of the FG loop (FIG. 1) and, thus, it is expected that these modification will have little, if any, effect on the binding activity of FN3 mutants.

Streptavidin will be cross-linked with the dextran coat of the SPIO particles by chemical modification (reductive amination) (Shen et al., 1996). Then, biotinylated FN3 will be attached to this complex, and FN3-biotin-streptavidin-SPIO will be purified using ultrafiltration.

REFERENCES

Each of the references cited herein or otherwise listed below are expressly incorporated by reference in their entirety into this specification.

Adonis et al. (1994) *Amer. J. Ophthal.* 118, 445-450.
Altroff et al. (2001) *J. Biol. Chem.* 276, 38885-38892.
Aukhil et al. (1993) *J. Biol. Chem.* 268, 2542-2553.
Bangham et al. (1965) *J. Mol. Biol.* 13, 238-252.
Baron et al. (1991) *Trends Biochem. Sci.* 16, 13-17.
Berkner, (1988) *Biotechniques* 6, 616-627.
Bennett et al. (1983) *Proc. Natl. Acad. Sci. USA,* 80, 2417-2421.
Blystone et al. (1994) *J. Cell Biol.* 127, 1129-1137.
Bork & Doolittle (1992) *Proc. Natl. Acad. Sci. USA* 89, 8990-8994.
Bork et al. (1994) *J. Mol. Biol.* 242, 309-320.
Brooks et al. (1994a) *Cell* 79, 1157-1164.
Brooks et al. (1994b) *Science* 264, 569-571.
Brooks et al. (1995) *J. Clin. Invest.* 96, 1815-1822.
Brooks et al. (1996) *Cell* 85, 683-693.
Campbell & Spitzfaden (1994) *Structure* 2, 333-337.
Carr et al. (1997) *Structure* 5, 949-959.
Chappel et al. (1998) *J. Immunol. Methods* 221, 25-34.
Chatterjee et al. (2000) *J. Neurooncol.* 46, 135-144.
Chatterjee et al. (2001) *Clin. Cancer Res.* 7, 3006-3011.
Choi et al. (1994) *J. Vasc. Surg.* 19(1), 125-134.
Deng & Nickoloff(1992) *Anal. Biochem.* 200, 81-88.
de Vos et al. (1992) *Science* 255, 306-12.
Dickinson et al. (1994) *J. Mol. Biol.* 236, 1079-1092.
Fisher et al. (1993) *Endocrinology* 132, 1411-1413.
Flotte et al. (1993) *Proc. Nat'l Acad. Sci. USA* 90, 10613-10617.
Friedlander et al. (1995) *Science* 270, 1500-1502.
Ghosh et al. (1995) *Nature* 373, 303-310.
Ginsberg et al. (1983) *J. Clin. Invest.,* 71, 619-624.
Gribskov et al. (1984) *Nucl. Acids Res.* 12, 539-549.
Haisma et al. (2000) *Cancer Gene Ther.* 7, 901-904.
Hantgan et al. (1992) *Thromb. Haemost.* 68, 694-700.
Harbottle et al. (1998) *Hum. Gene Ther.* 9, 1037-1047.
Harpez & Chothia (1994) *J. Mol. Biol.* 238, 528-539.
Hart (1999) *Curr. Opin. Mol. Ther.* 1, 197-203.
Healy et al. (1995) *Biochemistry* 34, 3948-3955.
Horton (1997) *Int. J. Biochem. Cell Biol.* 29, 721-725.
Hufton et al. (2000) *FEBS Lett.* 475, 225-231.
Humphries et al. (1988) *J Clin. Invest.* 81, 782-790.
Jones (1993) *Curr. Opinion Struct. Biol.* 3, 846-852.
Kabalka et al. (1991) *Magn. Reson. Med.* 19, 406-15.
Kaplitt et al. (1994) *Nature Genet.* 8,148-153.
Kayyem et al. (1995) *Chem. Biol.* 2, 615-20.
Koide et al. (1998) *J. Mol. Biol.* 284, 1141-1151.
Koide et al. (2001) *Biochem.* 40, 10326-10333.
Koivunen et al. (1994) *Methods Enzymol.* 245, 346-369.
Kozlova et al. (2001) *Oncogene* 20, 4710-4717.
Kraulis (1991) *J. Appl. Cryst.* 24, 946-950.
Kresse et al. (1998) *Magn. Reson. Med.* 40, 236-42.
Kumar et al. (1997) *J. Pharmacol. Exp. Ther.* 283, 843-853.
Kunkel (1985) *Proc. Natl. Acad. Sci. USA* 82, 488-492.
Kunkel et al. (1987) *Methods Enzymol.* 154, 367-382.
Leahy et al. (1992) *Science* 258, 987-991.
Main et al. (1992) *Cell* 71, 671-678.
Marcinkiewicz et al. (2000) *J. Biol. Chem.* 275, 31930-31937.
McLane et al. (1996) *FEBS Lett.* 391, 139-143.
Montgomery et al. (1994) *Proc. Natl. Acad. Sci. USA* 91, 8856-8860.
Moore et al. (2000) *Radiology* 214, 568-74.
Müller et al. (1995) *Nature* 373, 311-117.
Ondrick et al. (1992) *Clin. Podiatr. Med. Surg.* 9, 185-202.
Pampori et al. (1999) *J. Biol. Chem.* 274, 21609-21616.
Peacock et al. (1992) *J. Exp. Med.* 175, 1135-1138.
Reimer et al. (1991) *Radiology* 180, 641-645.
Reimer et al. (1992) *J. Magn. Reson. Imaging* 2, 177-81.
Reimer et al. (1994) *Radiology* 193, 527-531.
Roberts & Lauer (1979) *Methods in Enzymology* 68, 473-482.
Rosenfeld et al. (1991) *Science* 252, 431-434.
Ruggeri et al. (1982) *Proc. Natl. Acad. Sci. USA,* 79, 6038-6041.
Sambrook et al. (1989) *Molecular Cloning: A laboratory manual, 2nd Ed.* (Cold Spring Harbor Laboratory, Cold Spring Harbor).
Sandhu et al. (1992) *BioTech* 12, 14-16.
Sato et al. (1990) *J. Cell. Biol.* 111, 1713-1723.
Scarborough et al. (1993) *J. Biol. Chem.* 268, 1058-1065.
Schaffer et al. (1993) *Magn. Reson. Imaging* 11, 411-417.
Seftor et al. (1992) *Proc. Natl. Acad. Sci. USA* 89, 1557-1561.
Shen et al. (1996) *Bioconjug. Chem.* 7, 311-316.
Silletti et al. (2001) *Proc. Natl. Acad. Sci. USA* 98, 119-124.
Sipkins et al. (1998) *Nat. Med.* 4, 623-626.
Small et al. (1994) *J. Magn. Reson. Imaging* 4, 325-330.
Suwa et al. (1998) *Int. J. Cancer* 75, 626-634.
Tilcock et al. (1992) *Magn. Reson. Med.* 27, 44-51.
Trubetskoy et al. (1992) *Bioconjug. Chem.* 3, 323-327.
Vera et al. (1995) *Acad. Radiol.* 2, 497-506.
Wang & Huang (1987) *Proc. Natl. Acad. Sci. USA* 84, 7851-7855.
Weidner (1993) *Semin. Diagn. Pathol.* 10, 302-313.
Weiss et al. (2001) *J. Exp. Med.* 194, 1219-1229.
White (1993) *Current Biology* 3(9), 596-599.
Wickham et al. (1997) *Cancer Immunol. Immunother.* 45, 149-151.
Wickham et al. (1996) J. Virol. 70, 6831-6838.
Williams & Barclay (1988) *Ann. Rev. Immunol.* 6, 381-405.
Wu & Wu (1987) *J. Biol. Chem.* 262, 4429-4432.
Wu & Wu (1988) *J. Biol. Chem.* 263, 14621-14624.
Zhou et al. (1991) *Biochim. Biophys. Acta* 1065, 8-14.
U.S. Pat. No. 6,057,155 to Wickham et al.

U.S. Pat. No. 6,033,908 to Bout et al.
U.S. Pat. No. 6,001,557 to Wilson et al.
U.S. Pat. No. 5,994,132 to Chamberlain et al.
U.S. Pat. No. 5,981,225 to Kochanek et al.
U.S. Pat. No. 5,885,808 to Spooner et al.
U.S. Pat. No. 5,885,613 to Holland et al.
U.S. Pat. No. 5,871,727 to Curiel
U.S. Pat. No. 5,849,586 to Kriegler et al.
U.S. Pat. No. 5,681,811 to Ekwuribe
U.S. Pat. No. 5,653,996 to Hsu et al.
U.S. Pat. No. 5,643,599 to Lee et al.
U.S. Pat. No. 5,631,237 to Dzau et al.
U.S. Pat. No. 5,059,421 to Loughrey et al.
U.S. Pat. No. 4,237,224 to Cohen and Boyer Although the invention has been described in detail for the purposes of illustration, it is understood that such detail is solely for that purpose, and variations can be made therein by those skilled in the art without departing from the spirit and scope of the invention which is defined by the following claims.

---

What is claimed:

1. A fibronectin type III (Fn3) polypeptide monobody derived from the amino acid sequence of SEQ ID NO: 2 or SEQ ID NO: 3, the polypeptide monobody comprising:
   at least two adjacent Fn3 β-strand domain sequences selected from the group of A-G with a loop region sequence linked between adjacent β-strand domain sequences, the loop region sequence being selected from the group of loops AB, BC, CD, DE, EF, and FG; and
   optionally, an N-terminal tail of at least about 2 to about 25 amino acids, a C-terminal tail of at least about 2 to about 25 amino acids, or both;
   wherein:
      at least one loop region sequence, selected from the group of AB, BC, CD, DE, and FG loop region sequences, comprises a modified amino acid sequence which varies from a corresponding loop region sequence present in SEQ ID NO:2 or 3 by deletion of up to all but one amino acid residue, insertion of two to about 25 amino acid residues, or replacement of two to substantially all amino acid residues,
      one modified amino acid sequence comprises RGDWXE (residues 2-7 of SEQ ID No: 26), and
      wherein the polypeptide monobody binds selectively to αvβ3 integrin.

2. The polypeptide monobody according to claim 1, wherein the one modified amino acid sequence comprises XRGDWXEX where X is any amino acid (SEQ ID No: 26).

3. The polypeptide monobody according to claim 2, wherein the one modified amino acid sequence comprises LRGDWSED (SEQ ID No: 5), VRGDWYEY (SEQ ID No: 6), GRGDWTEH (SEQ ID No: 10), ARGDWVEG (SEQ ID No: 11), PRGDWTEG (SEQ ID No: 12), PRGDWIEF (SEQ ID No: 15), PRGDWNEG (SEQ ID No: 23), or FRGDWIEL (SEQ ID No: 24).

4. The polypeptide monobody according to claim 1, wherein the loop region sequence that comprises the modified amino acid sequence comprising RGDWXE (residues 2-7 of SEQ ID No: 26) is selected from the group consisting of a BC loop region sequence, a DE loop region sequence, and an FG loop region sequence.

5. The polypeptide monobody according to claim 4, wherein the loop region sequence that comprises the modified amino acid sequence comprising RGDWXE (residues 2-7 of SEQ ID No: 26) is an FG loop region sequence.

6. The polypeptide monobody according to claim 5, wherein the FG loop region sequence comprises, as the modified amino acid sequence, XRGDWXEX where X is any amino acid (SEQ ID No: 26).

7. The polypeptide monobody according to claim 6, wherein the modified amino acid sequence comprises LRGDWSED (SEQ ID No: 5), VRGDWYEY (SEQ ID No: 6), GRGDWTEH (SEQ ID No: 10), ARGDWVEG (SEQ ID No: 11), PRGDWTEG (SEQ ID No: 12), PRGDWIEF (SEQ ID No: 15), PRGDWNEG (SEQ ID No: 23), or FRGDWIEL (SEQ ID No: 24).

8. A fusion protein comprising:
   a polypeptide monobody according to claim 1 and
   a second polypeptide linked by peptide bond to the polypeptide monobody, the second polypeptide being (i) an epitope tag polypeptide, (ii) a detectable marker polypeptide, (iii) a metal ion-complexing polypeptide, or (iv) a DNA-binding polypeptide.

9. The fusion protein according to claim 8 wherein the one modified amino acid sequence comprises XRGDWXEX (SEQ ID No: 26) where X is any amino acid.

10. The fusion protein according to claim 8 wherein the second polypeptide is an epitope tag polypeptide.

11. The fusion protein according to claim 10 wherein the epitope tag comprises a polyhistidine amino acid sequence.

12. The fusion protein according to claim 8 wherein the second polypeptide is a detectable marker polypeptide.

13. The fusion protein according to claim 12 wherein the detectable marker polypeptide is an alkaline phosphatase.

14. The fusion protein according to claim 8 wherein the second polypeptide is a metal ion-complexing polypeptide.

15. The fusion protein according to claim 14 wherein the metal-ion complexing polypeptide is a polyhistidine amino acid sequence.

16. The fusion protein according to claim 8 wherein the second polypeptide is a DNA-binding polypeptide.

17. The fusion protein according to claim 16 wherein the DNA-binding polypeptide comprises a polylysine amino acid sequence.

18. A fusion protein-metal ion complex comprising a fusion protein according to claim 14 which is complexed with a metal ion.

19. The fusion protein-metal ion complex according to claim 18 wherein the metal ion is a positron emitting metal ion, a paramagnetic metal ion, a radioactive metal ion, or a non-radioactive metal ion.

20. The fusion protein-metal ion complex according to claim 18 wherein the one modified amino acid sequence comprises XRGDWXEX where X is any amino acid (SEQ ID No: 26).

21. A conjugate comprising a polypeptide monobody according to claim 1 conjugated to (i) a chemotherapeutic agent, (ii) a contrasting agent, or (iii) an organic chelating agent.

22. The conjugate according to claim 21 wherein the one modified amino acid sequence comprises XRGDWXEX where X is any amino acid (SEQ ID No: 26).

23. The conjugate according to claim 21 wherein the polypeptide monobody is conjugated to a chemotherapeutic agent.

24. The conjugate according to claim 21 wherein the polypeptide monobody is conjugated to a contrasting agent or an organic chelating agent.

25. The conjugate according to claim 24, wherein the contrasting agent is a dextran-coated superparamagnetic iron oxide particle, a lipid vesicle with $Gd^{3+}$ attached to a surface thereof, or poly-lysine with $Gd^{3+}$ attached to an amino group thereof.

26. The conjugate according to claim 24, wherein the organic chelating agent is diethylenetriamine pentaacetic acid.

27. A composition comprising a pharmaceutically acceptable carrier and a polypeptide monobody according to claim 1.

28. A composition comprising a pharmaceutically acceptable carrier and the fusion protein according to claim 8.

29. A composition comprising a pharmaceutically acceptable carrier and the conjugate according to claim 21.

30. A method of inhibiting $\alpha v \beta 3$ integrin activity comprising:
contacting $\alpha v \beta 3$ integrin with a polypeptide monobody according to claim 1 under conditions effective to inhibit the activity of the $\alpha v \beta 3$ integrin.

31. The method according to claim 30 wherein the one modified amino acid sequence comprises XRGDWXEX where X is any amino acid (SEQ ID No: 26).

* * * * *